United States Patent
Weber et al.

(10) Patent No.: US 9,526,814 B2
(45) Date of Patent: Dec. 27, 2016

(54) MEDICAL BALLOONS AND METHODS OF MAKING THE SAME

(75) Inventors: Jan Weber, Maple Grove, MN (US); Liliana Atanasoska, Edina, MN (US); Alexey Kondyurin, Sutherland (AU)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2228 days.

(21) Appl. No.: 11/355,392

(22) Filed: Feb. 16, 2006

(65) Prior Publication Data

US 2007/0191923 A1    Aug. 16, 2007

(51) Int. Cl.
*A61M 25/10*    (2013.01)
*A61L 31/08*    (2006.01)
*A61L 27/30*    (2006.01)

(52) U.S. Cl.
CPC .......... *A61L 31/084* (2013.01); *A61L 27/303* (2013.01)

(58) Field of Classification Search
USPC ........................................ 623/1.11; 424/423
See application file for complete search history.

(56) References Cited

U.S. PATENT DOCUMENTS

| | | | |
|---|---|---|---|
| 4,490,421 A | 12/1984 | Levy | |
| 4,963,313 A | 10/1990 | Noddin et al. | |
| 5,047,045 A | 9/1991 | Arney et al. | |
| 5,190,807 A * | 3/1993 | Kimock et al. | 428/216 |
| 5,195,969 A | 3/1993 | Wang et al. | |
| 5,270,086 A | 12/1993 | Hamlin | |
| 5,290,306 A * | 3/1994 | Trotta et al. | 606/194 |
| 5,348,538 A | 9/1994 | Wang et al. | |
| 5,366,442 A | 11/1994 | Wang et al. | |
| 5,403,340 A | 4/1995 | Wang et al. | |
| 5,447,497 A | 9/1995 | Sogard et al. | |
| 5,556,383 A | 9/1996 | Wang et al. | |
| 5,593,719 A | 1/1997 | Dearnaley et al. | |
| 5,609,629 A | 3/1997 | Fearnot et al. | |
| 5,705,233 A | 1/1998 | Denes et al. | |
| 5,725,573 A | 3/1998 | Dearnaley et al. | |
| 5,766,618 A | 6/1998 | Laurencin et al. | |
| 5,830,182 A | 11/1998 | Wang et al. | |
| 5,908,539 A | 6/1999 | Young et al. | |
| 5,945,153 A | 8/1999 | Dearnaley | |
| 5,951,941 A | 9/1999 | Wang et al. | |
| 6,054,018 A | 4/2000 | Denes et al. | |
| 6,082,292 A | 7/2000 | Denes et al. | |
| 6,096,564 A | 8/2000 | Denes et al. | |
| 6,120,260 A | 9/2000 | Jirele | |
| 6,171,278 B1 * | 1/2001 | Wang et al. | 604/104 |

(Continued)

FOREIGN PATENT DOCUMENTS

| | | | |
|---|---|---|---|
| EP | 0 302 717 A1 | 2/1989 | |
| EP | 0 567 285 B1 | 5/1995 | |

(Continued)

OTHER PUBLICATIONS www.calce.umd.edu/general/Facilities/hardness_ad_htm.*

(Continued)

*Primary Examiner* — Ryan J Severson
(74) *Attorney, Agent, or Firm* — Seager, Tufte & Wickhem, LLP

(57) ABSTRACT

Medical balloons are provided that have enhanced properties, such as enhanced puncture and scratch resistance.

28 Claims, 21 Drawing Sheets

(56) References Cited

U.S. PATENT DOCUMENTS

| | | |
|---|---|---|
| 6,171,287 B1 | 1/2001 | Lynn et al. |
| 6,290,721 B1 | 9/2001 | Heath |
| 6,335,029 B1 | 1/2002 | Kamath et al. |
| 6,406,457 B1 | 6/2002 | Wang et al. |
| 6,432,134 B1 | 8/2002 | Anson et al. |
| 6,500,174 B1 | 12/2002 | Maguire et al. |
| 6,517,888 B1 | 2/2003 | Weber |
| 6,531,182 B2 | 3/2003 | Veerasamy et al. |
| 6,547,804 B2 | 4/2003 | Porter et al. |
| 6,549,811 B2 | 4/2003 | Stewart et al. |
| 6,562,445 B2 | 5/2003 | Iwamura |
| 6,572,651 B1 | 6/2003 | De Scheerder et al. |
| 6,585,926 B1 | 7/2003 | Mirzaee |
| 6,592,519 B1 | 7/2003 | Martinez |
| 6,592,550 B1 | 7/2003 | Boatman et al. |
| 6,599,462 B1 | 7/2003 | Miraki |
| 6,660,340 B1 | 12/2003 | Kirkpatrick |
| 6,696,157 B1 | 2/2004 | David et al. |
| 6,709,463 B1 | 3/2004 | Pope et al. |
| 6,720,402 B2 | 4/2004 | Langer et al. |
| 6,726,712 B1 | 4/2004 | Raeder-Devens et al. |
| 6,733,513 B2 | 5/2004 | Boyle et al. |
| 6,753,071 B1 | 6/2004 | Pacetti |
| 6,761,736 B1* | 7/2004 | Woo et al. ............ 623/2.42 |
| 6,908,506 B2 | 6/2005 | Zimmermann |
| 6,939,320 B2 | 9/2005 | Lennox |
| 6,951,675 B2 | 10/2005 | Chin et al. |
| 6,953,560 B1 | 10/2005 | Castro et al. |
| 6,953,594 B2 | 10/2005 | Lee et al. |
| 2002/0004060 A1 | 1/2002 | Heublein et al. |
| 2002/0026899 A1 | 3/2002 | McLaughlin et al. |
| 2002/0082638 A1 | 6/2002 | Porter et al. |
| 2003/0015284 A1 | 1/2003 | Merdan et al. |
| 2003/0069632 A1 | 4/2003 | De Scheerder et al. |
| 2003/0104028 A1 | 6/2003 | Hossainy et al. |
| 2003/0221307 A1 | 12/2003 | Kaese et al. |
| 2004/0047909 A1 | 3/2004 | Ragheb et al. |
| 2004/0148007 A1 | 7/2004 | Jackson et al. |
| 2004/0210211 A1 | 10/2004 | Devens, Jr. et al. |
| 2004/0219294 A1* | 11/2004 | Massler et al. ............ 427/249.1 |
| 2005/0010275 A1 | 1/2005 | Sahatjian et al. |
| 2005/0033418 A1 | 2/2005 | Banas et al. |
| 2005/0079201 A1* | 4/2005 | Rathenow et al. ............ 424/424 |
| 2005/0208098 A1* | 9/2005 | Castro et al. ............ 424/423 |
| 2005/0216074 A1 | 9/2005 | Sahatjian et al. |
| 2005/0249777 A1 | 11/2005 | Michal et al. |
| 2006/0079863 A1 | 4/2006 | Burgmeier et al. |

FOREIGN PATENT DOCUMENTS

| | | |
|---|---|---|
| EP | 0 567 285 B1 | 5/1998 |
| EP | 0 876 821 A2 | 11/1998 |
| EP | 0876821 | 11/1998 |
| EP | 1 754 684 | 2/2007 |
| GB | 2 287 473 | 3/1995 |
| GB | 2287473 | 9/1995 |
| JP | 59-192366 | 10/1984 |
| JP | 60-135062 | 7/1985 |
| JP | 11106920 | 4/1999 |
| JP | 2003000527 | 1/2003 |
| JP | 2003310744 | 11/2003 |
| JP | 2007195883 | 8/2007 |
| WO | WO 01/43790 A2 | 6/2001 |
| WO | WO 0143790 | 6/2001 |
| WO | WO 03/037223 A1 | 5/2003 |
| WO | WO 2005037985 | 4/2005 |
| WO | WO 2005/097673 | 10/2005 |

OTHER PUBLICATIONS

Maitz et al., "Surface Modification of ePTFE and Implants Using the Same", U.S. Appl. No. 11/227,378, filed Sep. 15, 2005.

Rao et al., "The characterisation of e-beam evaporated and magnetron sputtered carbon films fabricated for atomic oxygen sensors", Surface & Coatings Technology, 197, pp. 154-160, 2005.

Kondyurin et al., "Pulse and continuous ion beam treatment of polyethylene", Vacuum, 68, pp. 341-347, 2003.

Kondyurin et al., "Plasma immersion ion implantation of polyethylene", Vacuum, 64, 105-111, 2002.

Curriculum Vitae of Dr. Alexey Kondyurin, including, "Ion Beam Treatment of Polymers (IBT)", downloaded Nov. 3, 2005.

Weber et al., "Bioerodible Endoprostheses and Methods of Making the Same", U.S. Appl. No. 11/355,368, filed Feb. 16, 2006.

Weber, "Bioerodible Endoprostheses and Methods of Making the Same", U.S. Appl. No. 11/327,149, filed Jan. 5, 2006.

Prikryl et al., "Mechanical and optical properties of plasma-polymerized vinyltriethoxysilane", Surface and Coatings Technology, vol. 200, pp. 468-471, 2005.

Kutsenko et al., "Structural changes in Mg alloy induced by plasma immersion ion implantation of Ag", Acta Materialia, vol. 52, pp. 4329-4335, 2004.

Günzel et al., "Basic investigations of an integrated modulator for plasma immersion ion implantation", Surface and Coatings Technology, vol. 136, pp. 47-50, 2001.

R. Günzel, "Integrated high voltage modulator for plasma immersion ion implantation", J. Vac. Sci. Technol. B, vol. 17, No. 2, pp. 895-899, Mar./Apr. 1999.

Brückner et al., "Metal plasma immersion ion implantation and deposition (MPIIID): chromium on magnesium", Suface and Coatings Technology, vol. 103-104, pp. 227-230, 1998.

Shiao, et al., Thin Solid Films, vol. 283, pp. 145-150, 1996.

Valenza et al., "Characterization of ultra-high-molecular-weight polyethylene (UHMWPE) modified by ion implantation" *Polymer, Elsevier Science Publishers B.V.*, GB, vol. 45, No. 5: pp. 1707-1715 (2004).

Bilek et al., "The role of energetic ions from plasma in the creation of nanostructured materials and stable polymer surface treatments" *Nuclear Instruments & Physics Research, Section-B: Beam Interactions with Materials and Atoms*, Elsevier, Amsterdam, NL, vol. 242, No. 1-2: pp. 221-227 (2006).

NASA Tech Briefs: "Fluorinated Diamondlike Carbon Coatings", Copyright Oct. 2001, 1 page. http://www.findarticles.com/p/articles/mi_qa3957/is_200110/ai_n8967401/print.

J. Robertson, "Diamond-Like Carbon," Pure & Appl. Chem., 1994, vol. 66, No. 9, pp. 1789-1796.

H. Schittenhelm, et al. "Synthesis and Characterization of Single-Wall Carbon Nanotube-Amorphous Diamond Thin-Film Composites," Applied Physics Letters, vol. 81, No. 11, Sep. 9, 2002, pp. 2097-2099.

\* cited by examiner

MEDICAL BALLOONS AND METHODS OF MAKING THE SAME

TECHNICAL FIELD

This disclosure relates to medical balloons, and to methods of making the same.

BACKGROUND

The body includes various passageways such as arteries, other blood vessels, and other body lumens. These passageways sometimes become occluded, e.g., by a tumor or restricted by plaque. To widen an occluded body vessel, balloon catheters can be used, e.g., in angioplasty.

A balloon catheter can include an inflatable and deflatable balloon carried by a long and narrow catheter body. The balloon is initially folded around the catheter body to reduce the radial profile of the balloon catheter for easy insertion into the body.

During use, the folded balloon can be delivered to a target location in the vessel, e.g., a portion occluded by plaque, by threading the balloon catheter over a guide wire emplaced in the vessel. The balloon is then inflated, e.g., by introducing a fluid into the interior of the balloon. Inflating the balloon can radially expand the vessel so that the vessel can permit an increased rate of blood flow. After use, the balloon is deflated and withdrawn from the body.

In another technique, the balloon catheter can also be used to position a medical device, such as a stent or a stent-graft, to open and/or to reinforce a blocked passageway. For example, the stent can be delivered inside the body by a balloon catheter that supports the stent in a compacted or reduced-size form as the stent is transported to the target site. Upon reaching the site, the balloon can be inflated to deform and to fix the expanded stent at a predetermined position in contact with the lumen wall. The balloon can then be deflated and the catheter withdrawn. Stent delivery is further discussed in Heath, U.S. Pat. No. 6,290,721, the entire disclosure of which is hereby incorporated by reference herein.

One common balloon catheter design includes a coaxial arrangement of an inner tube surrounded by an outer tube. The inner tube typically includes a lumen that can be used for delivering the device over a guide wire. Inflation fluid passes between the inner and outer tubes. An example of this design is described in Arney, U.S. Pat. No. 5,047,045, the entire contents of which is hereby incorporated by reference herein.

In another common design, the catheter includes a body defining a guide wire lumen and an inflation lumen arranged side-by-side. Examples of this arrangement are described in Wang, U.S. Pat. No. 5,195,969, the entire contents of which is hereby incorporated by reference herein.

SUMMARY

In one aspect, the disclosure features a medical balloon that includes a balloon wall having a base polymer system with an integral modified region including carbonized base polymer material.

In another aspect, the disclosure features a balloon catheter that includes a balloon wall having a base polymer system with an integral modified region including a carbonized base polymer material.

In another aspect, the disclosure features a method of making a medical balloon that includes providing a polymer system; treating the polymer system by plasma immersion ion implantation; and utilizing the treated polymer system in a medical balloon.

In another aspect, the disclosure features a method of making a medical balloon that includes providing a polymer system; treating the polymer system by ion implantation to modify the polymer system without substantial deposition of non-polymer system material; and utilizing the treated system in a medical balloon.

In another aspect, the disclosure features a medical balloon formed by any of the above described methods.

In another aspect, the disclosure features a medical device that includes a base polymer system including coextruded polymers, the base polymer system having an integral modified region of carbonized base polymer system material.

In another aspect, the disclosure features medical balloons which exhibit a D peak and/or a G peak in Raman.

Other aspects or embodiments may include combinations of the features in the aspects above and/or one or more of the following. The carbonized region includes diamond-like material and/or the carbonized region includes graphitic material. The modified region includes a region of crosslinked base polymer material. The crosslinked region is directly bonded to the carbonized base polymer material and to substantially unmodified base polymer material. The medical balloon can include a region of oxidized base polymer material, the oxidized region being directly bonded to the carbonized material without further bonding to the base polymer system. The modified region extends from an exposed surface of the base polymer system. The modulus of elasticity of the base polymer system is within about +/−10% of the base polymer system without the modified region. The thickness of the modified region is about 10 to about 200 nm. The modified region is about 1% or less of the overall thickness of the base polymer system. A hardness coefficient of the carbonized base polymer material is about 500 Vickers Hardness (kgf/mm$^2$) or more. The balloon has a fractured surface morphology having a surface fracture density of about five percent or more. The base polymer system carries a therapeutic agent. The base polymer system includes coextruded polymer layers. A compliancy of the balloon is less than 10 percent of an initial diameter of the balloon between an internal pressure from about 2 bar to about 15 bar. The balloon catheter is sized for use in the vascular system. The balloon catheter is sized for use in the coronary arteries. The balloon catheter includes a stent positioned over the balloon. The ion energy and dose is controlled to form a carbonized region in the polymer system. The ion energy in a range of about 15 keV or more and a dose of about $1\times10^{15}$ ions/cm$^2$ or more. A stent is about the medical balloon. The treating of the polymer system utilizes an ion selected from the group consisting of hydrogen, helium, boron, neon, carbon, oxygen, nitrogen, argon, or mixtures of these. The modified region includes an interface of coextruded polymers.

All publications, patent applications, patents, and other references mentioned herein are incorporated by reference herein in their entirety.

Embodiments may have one or more of the following advantages. A balloon is provided in which properties, such as puncture resistance, scratch resistance, flexibility, burst strength, and drug release, are enhanced for a given application. In particular, a stent delivery balloon is provided with a high scratch resistance. The scratch resistance of the balloon is enhanced by providing a balloon wall that includes a relatively hard region, e.g., including a diamondlike material (e.g., diamond like carbon or amorphous diamond), which is tightly adhered to a base polymer system.

Still further features, embodiments, and advantages follow.

DETAILED DESCRIPTION

Figure 1A:
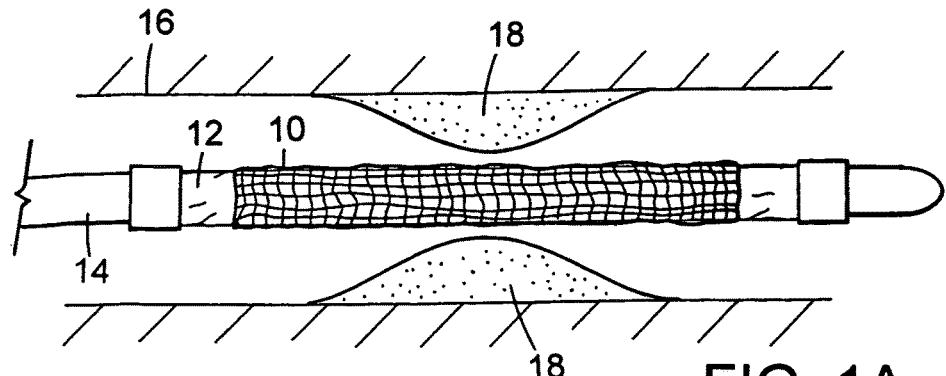
FIGS. 1A-1C are partial longitudinal cross-sectional views, illustrating delivery of a stent in a collapsed state, expansion of the stent, and deployment of the stent in a body lumen.
Figure 1B:
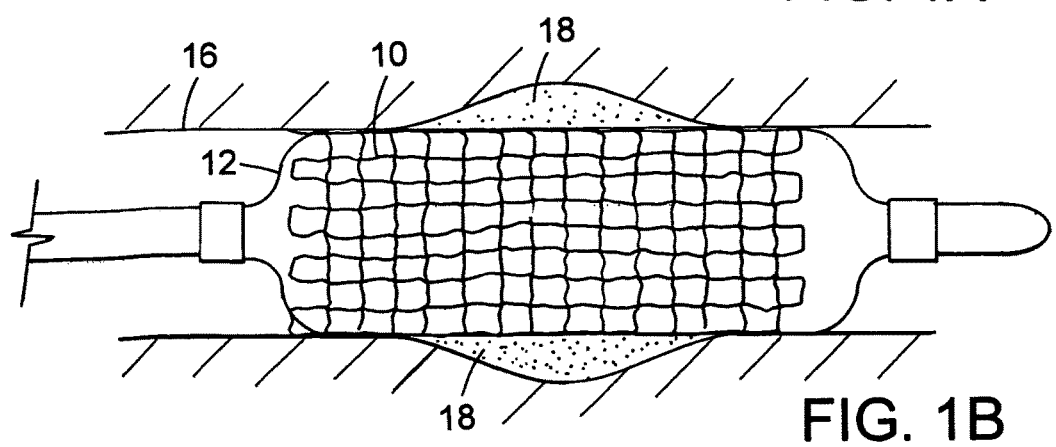
Figure 1C:
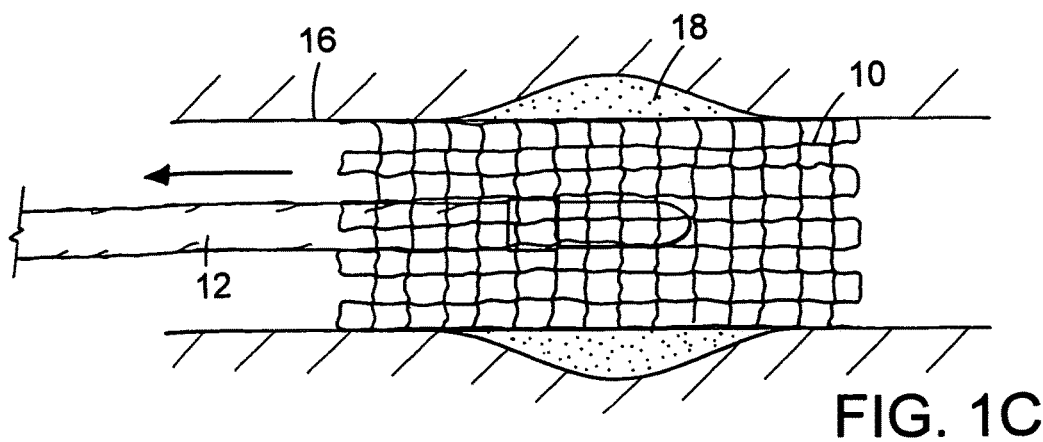

Referring to FIGS. 1A-1C, stent 10 is placed over a balloon 12 carried near a distal end of a catheter 14, and is directed through a lumen 16, e.g., a blood vessel such as the coronary artery, until the portion carrying the balloon and stent reaches the region of an occlusion 18 (FIG. 1A). The stent 10 is then radially expanded by inflating the balloon 12, and is pressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
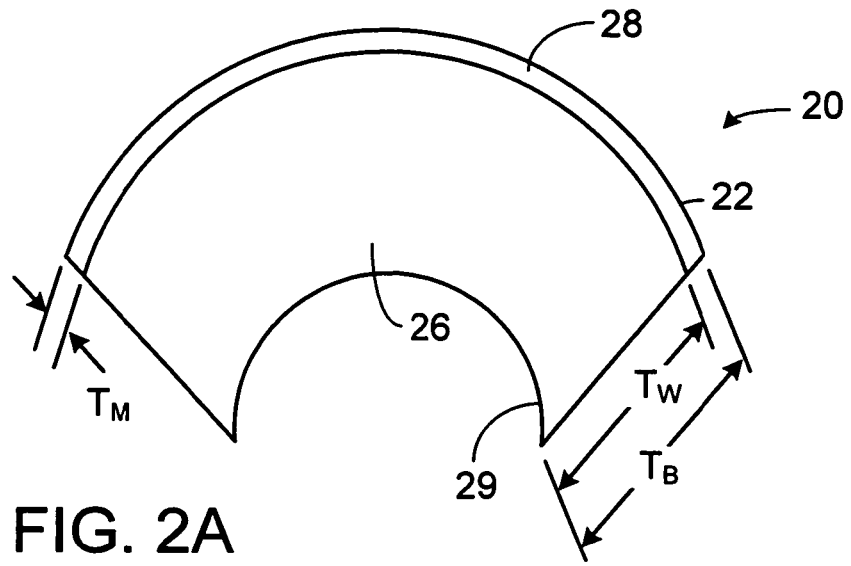
FIG. 2A is a transverse end on cross-sectional view through a wall of a balloon, showing an unmodified base polymer system region and a hard base polymer modified region.

Referring to FIG. 2A, balloon wall 20 having overall thickness $T_W$ includes an outer surface 22 adjacent to the stent and an inner surface 29 exposed to inflation fluid in the balloon interior. The balloon wall is formed of a base polymer system including an unmodified region 26 and a hard, modified region 28 of thickness $T_M$. The unmodified base polymer has a thickness $T_B$ that is the difference between the overall wall thickness $T_W$ and thickness $T_M$ of the modified region.

Figure 2B:
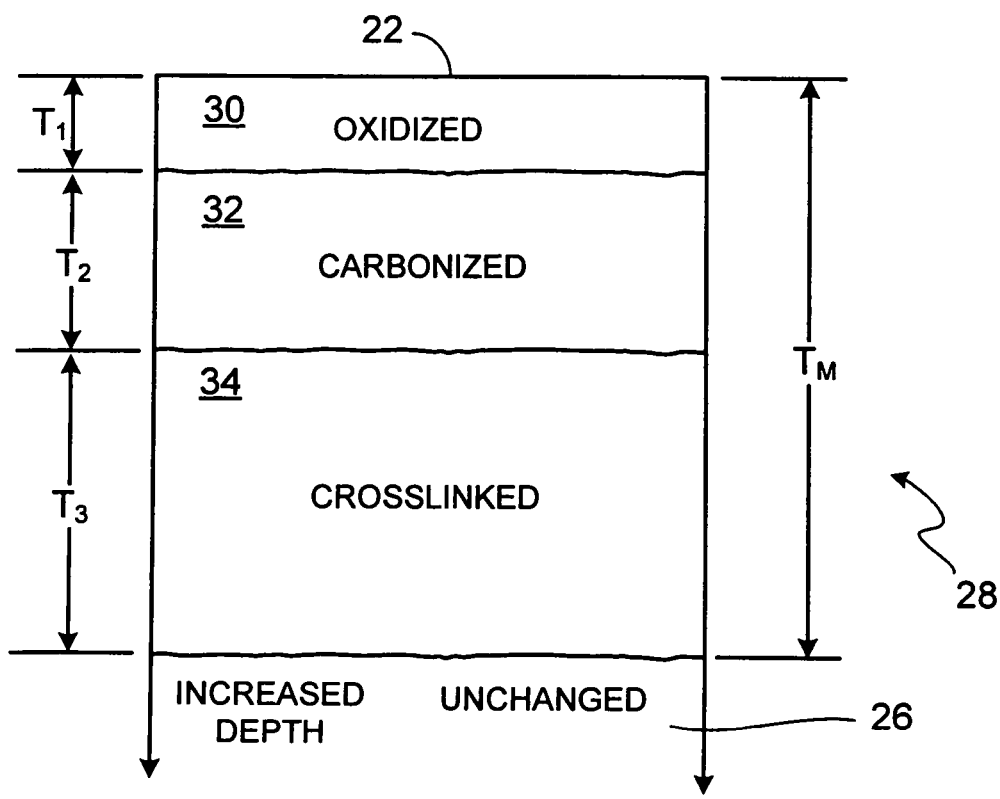
FIG. 2B is a schematic illustration of the compositional makeup of a portion of the balloon wall illustrated in FIG. 2A.

Referring to FIG. 2B, the modified region has a series of sub-regions, including an oxidized region 30 (e.g., having carbonyl groups, aldehyde groups, carboxylic acid groups and/or alcohol groups), a carbonized region 32 (e.g., having increased $sp^2$ bonding, particularly aromatic carbon-carbon bonds and/or $sp^3$ diamond-like carbon-carbon bonds), and a crosslinked region 34. In particular embodiments, the crosslinked region 34 is a region of increased polymer crosslinking that is bonded directly to the unmodified base polymer system and to the carbonized region 32. The carbonized region 32 is a band that typically includes a high-level of $sp^3$-hybridized carbon atoms, e.g., greater than 25 percent $sp^3$, greater than 40 percent, or even greater than 50 percent $sp^3$-hyridized carbon atoms, such as exists in diamond-like carbon (DLC). The oxidized region 30 that is bonded to the carbonized layer 32 and exposed to atmosphere includes an enhanced oxygen content, relative to the base polymer system. The hard, scratch resistant nature of the carbonized region reduces pinhole formation, which can occur, e.g., during crimping of stents. For example, a dust particle disposed between the stent and an outer balloon surface can be compressed into the balloon during the crimping, penetrating the balloon and forming a pinhole. The graduated multi-region structure of the modified region enhances adhesion of the modified layer to the unmodified base polymer, reducing the likelihood of delamination. In addition, the graduated nature of the structure and low thickness of the modified region relative to the overall wall thickness enables the balloon to substantially maintain mechanical properties of the unmodified balloon. The presence of various regions, e.g., carbonized regions, oxidized regions, and crosslinked regions, can be detected using, e.g., infrared, Raman and UV-vis spectroscopy. For example, Raman spectroscopy measurements are sensitive to changes in translational symmetry and are often useful in the study of disorder and crystallite formation in carbon films. In Raman studies, graphite can exhibit a characteristic peak at 1580 $cm^{-1}$ (labeled 'G' for graphite). Disordered graphite has a second peak at 1350 $cm^{-1}$ (labeled 'D' for disorder), which has been reported to be associated with the degree of $sp^3$ bonding present in the material. The appearance of the D-peak in disordered graphite can indicate the presence in structure of six-fold rings and clusters, thus indicating the presence of $sp^3$ bonding in the material. XPS is another technique that has been used to distinguish the diamond phase from the graphite and amorphous carbon components. By deconvoluting the spectra, inferences can be made as to the type of bonding present within the material. This approach has been applied to determine the $sp^3/sp^2$ ratios in DLC material (see, e.g., Rao, *Surface & Coatings Technology* 197, 154-160, 2005, the entire disclosure of which is hereby incorporated by reference herein).

Figure 3A:
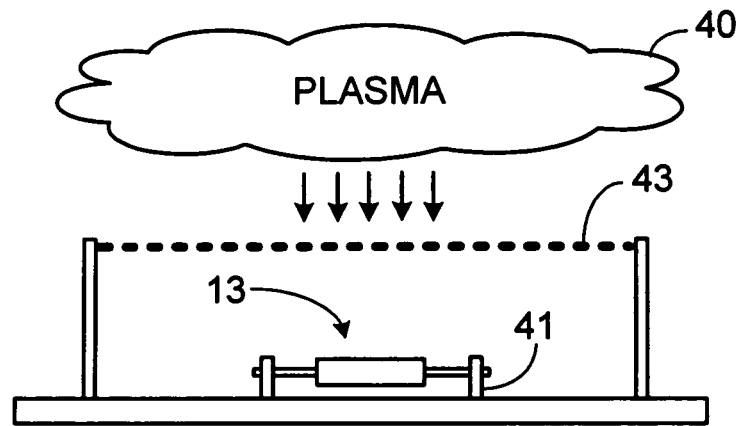
FIG. 3A is a schematic cross-sectional view of a plasma immersion ion implantation ("PIII") apparatus.
Figure 3B:
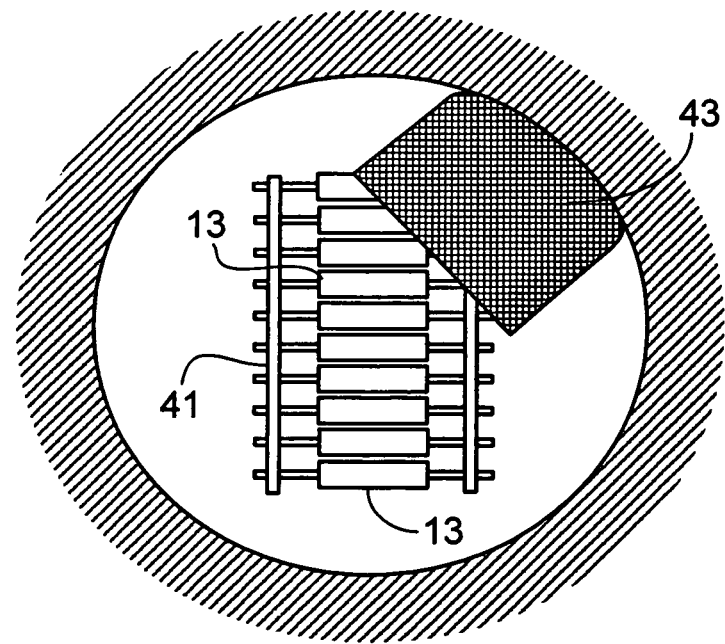
FIG. 3B is a schematic top view of ten balloons in a sample holder (metal grid electrode partially removed from view).

The balloon can be modified using plasma immersion ion implantation ("PIII"). Referring to FIGS. 3A and 3B, during PIII, charged species in a plasma 40, such as a nitrogen plasma, are accelerated at high velocity towards balloons 13 that are in a nominal, unexpanded state, and which are positioned on a sample holder 41. Acceleration of the charged species of the plasma towards the balloons is driven by an electrical potential difference between the plasma and an electrode under the balloon. Upon impact with a balloon, the charged species, due to their high velocity, penetrate a distance into the balloon and react with the material of the balloon, forming the regions discussed above. Generally, the penetration depth is controlled, at least in part, by the potential difference between the plasma and the electrode under the balloon. If desired, an additional electrode, e.g., in the form of a metal grid 43 positioned above the sample holder, can be utilized. Such a metal grid can be advantageous to prevent direct contact of the balloons with the rf-plama between high-voltage pulses and can reduce charging effects of the balloon material.

Figure 3C:
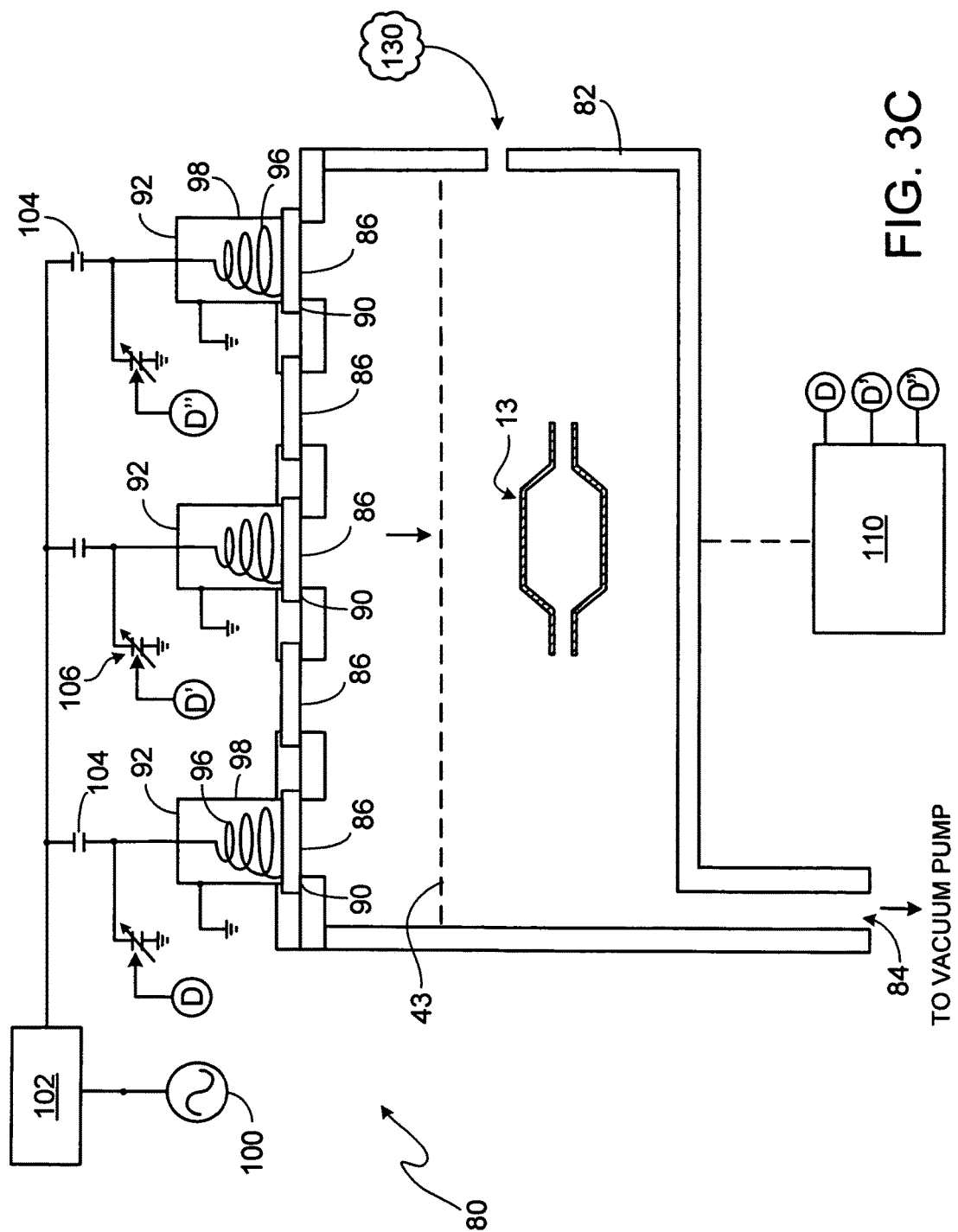
FIG. 3C is a detailed cross-sectional view of the plasma immersion ion implantation apparatus of FIG. 3A.

Referring toe FIG. 3C, an embodiment of a PIII processing system 80 includes a vacuum chamber 82 having a vacuum port 84 connected to a vacuum pump and a gas source 130 for delivering a gas, e.g., nitrogen, to chamber 82 to generate a plasma. System 80 includes a series of dielectric windows 86, e.g., made of glass or quartz, sealed by o-rings 90 to maintain a vacuum in chamber 82. Removably attached to some of the windows 86 are RF plasma sources 92, each source having a helical antenna 96 located within a grounded shield 98. The windows without attached RF plasma sources are usable, e.g., as viewing ports into chamber 82. Each antenna 96 electrically communicates with an RF generator 100 through a network 102 and a coupling capacitor 104. Each antenna 96 also electrically communicates with a tuning capacitor 106. Each tuning capacitor 106 is controlled by a signal D, D', D" from a controller 110. By adjusting each tuning capacitor 106, the output power from each RF antenna 96 can be adjusted to maintain homogeneity of the generated plasma. The regions of the balloons directly exposed to ions from the plasma can be controlled by rotating the balloons about their axis. The balloons can be rotated continuously during treatment to enhance a homogenous modification of the entire balloon. Alternatively, rotation can be intermittent, or selected regions can be masked to exclude treatment of those masked regions. Additional details of PIII is described by Chu, U.S. Pat. No. 6,120,260; Brukner, *Surface and Coatings Technology*, 103-104, 227-230 (1998); and Kutsenko, *Acta Materialia*, 52, 4329-4335 (2004), the entire disclosure of each of which is hereby incorporated by reference herein.

Balloon modification is controlled to produce a desired type of modification at a selected depth. The nature and depth of the modification is also controlled to adjust the overall mechanical properties of the balloon. In particular embodiments, the modification is controlled so that the mechanical properties, such as tensile strength, elongation and modulus of elasticity of the base polymer system are not substantially changed by the presence of the modification. In embodiments, the tensile strength, elongation and modulus of elasticity of the modified polymer is substantially the same as or greater than those respective values of the unmodified polymer. In addition, the modification is controlled so that balloon performance properties, such as burst strength, withdrawal force, torque and securement, are not substantially changed, or are improved by the presence of the modification.

The type and depth of modification is controlled in the PIII process by selection of the type of ion, the ion energy and ion dose. In embodiments, a three sub-region modification as described above is provided. In other embodiments, there may be more, or less than three sub-regions formed by controlling the PIII process parameters, or by post processing to remove one or more layers by, e.g., solvent dissolution, or mechanically removing layers by cutting, abrasion, or heat treating. In particular, a higher ion energy and dose enhances the formation of carbonized regions, particularly regions with DLC or graphitic components. In embodiments, the ion energy is about 5 keV or greater, such as 25 keV or greater, e.g. about 30 keV or greater and about 75 keV or less. The ion dosage in embodiments is in the range of about $1\times10^{14}$ or greater, such as $1\times10^{16}$ ions/cm$^2$ or greater, e.g. about $5\times10^{16}$ ions/cm$^2$ or greater, and about $1\times10^{19}$ ions/cm$^2$ or less. The oxidized region can be characterized, and the process conditions modified based on FTIR ATR spectroscopy results on carbonyl group and hydroxyl group absorptions. Also, the crosslinked region can be characterized using FTIR ATR spectroscopy, UV-vis spectroscopy and Raman spectroscopy by analyzing C=C group absorptions, and the process conditions modified based on the results. In addition, the process conditions can be modified based on an analysis of gel fraction of the crosslinked region, which can be determined using the principle that a crosslinked polymer is not soluble in any solvent, while a non-crosslinked polymer is soluble in a solvent. For example, the gel fraction of a sample can be determined by drying the sample in a vacuum oven at 50° C. until a constant weight is achieved, recording its initial dry weight, and then extracting the sample in a boiling solvent such as o-xylene for 24 hours using, e.g., a Soxhlet extractor. After 24 hours, the solvent is removed from the insoluble material, and then the insoluble material is further dried in a vacuum oven at 50° C. until a constant weight is achieved. The gel fraction is determined by dividing the dry weight of the insoluble material by the total initial dry weight of a sample.

In embodiments, the thickness $T_M$ of the modified region 28 is less than about 1500 nm, e.g., less than about 1000 nm, less than about 750 nm, less than about 500 nm, less than about 250 nm, less than about 150 nm, less than about 100 nm or less than about 50 nm. In embodiments, the oxidized region 30 can have a thickness $T_1$ of less than about 5 nm, e.g., less than about 2 nm or less than about 1 nm. In embodiments, the carbonized region 32 can have a thickness $T_2$ of less than about 500 nm, e.g., less than about 350 nm, less than about 250 nm, less than about 150 nm or less than about 100 nm, and can occur at a depth from outer surface 22 of less than about 10 nm, e.g., less than about 5 nm or less than 1 nm. In embodiments, the crosslinked region 34 has a thickness $T_3$ of less than about 1500 nm, e.g., less than about 1000 nm, or less than about 500 nm, and can occur at a depth from outer surface 22 of less than about 500 nm, e.g., less than about 350 nm, less than about 250 nm or less than about 100 nm.

In embodiments, burst strength, withdrawal force, torque and securement of the modified balloons are within about 35% or less, e.g. ±15%, e.g. ±5% or ±1% of those values for the unmodified balloon. In particular embodiments, withdrawal force and securement are increased by about 15% or more, e.g. about 25% or more by modification of the balloon wall. To minimize the influence of the modified region on overall mechanical properties of the balloon, the depth of the modification can be selected so that the mechanical properties of the modified region do not substantially affect the overall mechanical properties of the balloon. In embodiments, the thickness $T_M$ of the modified region is about 1% or less, e.g. about 0.5% or less or about 0.05% or more, of the thickness $T_B$ of the unmodified base polymer system. In embodiments, the balloon can be modified to vary the mechanical properties of the polymer or the balloon performance. For example, a balloon stiffness can be enhanced by modifying the balloon to include a relatively thick carbonized or crosslinked layer. In embodiments, the thickness $T_M$ of the modified layer can be about 25% or more, e.g. 50 to 90% of the overall thickness $T_B$ of the unmodified base polymer system. In embodiments, the wall has an overall thickness of less than about 0.005 inch, e.g., less than about 0.0025 inch, less than about 0.002 inch, less than about 0.001 inch or less than about 0.0005 inch.

In particular embodiments, the balloon is sized for use in the vascular system, such as the coronary arteries for angioplasty and/or stent delivery. The balloon has a burst strength of about 5 bar or more, e.g., about 15 bar or more. The base polymer system is, e.g., a polymer, a polymer blend, or layer structure of polymer that provides desirable properties to the balloon. In particular embodiments, the base polymer includes a low distendibility, high burst strength polymer. Polymers include biaxially oriented polymers, thermoplastic elastomers, engineering thermoplastic elastomers, polyethylenes, polyethylene terephthalate (PET), polybutylenes, polyamides (e.g. nylon 66), polyether block amides (e.g., PEBAX®), polypropylene (PP), polystyrene (PS), polyvinyl chlorides (PVC), polytetrafluorethylene (PTFE), polymethylmethacrylate (PMMA), polyimide, polycarbonate (PC), polyisoprene rubber (PI), nitrile rubbers, silicone rubbers, ethylene-propylene diene rubbers (EPDM), butyl rubbers (BR), thermoplastic polyurethanes (PU) (e.g., those based on a glycol ether and an isocyanate, such as PELLETHANE®). In particular embodiments, a poly(etheramide) block copolymer having the general formula

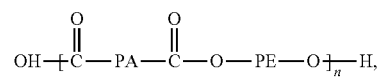

in which PA represents a polyamide segment, e.g., nylon 12, and PE represents a polyether segment, e.g., poly(tetramethylene glycol) is utilized. Such polymers are commercially available from ATOFINA under the tradename PEBAX®.

Figure 4A:
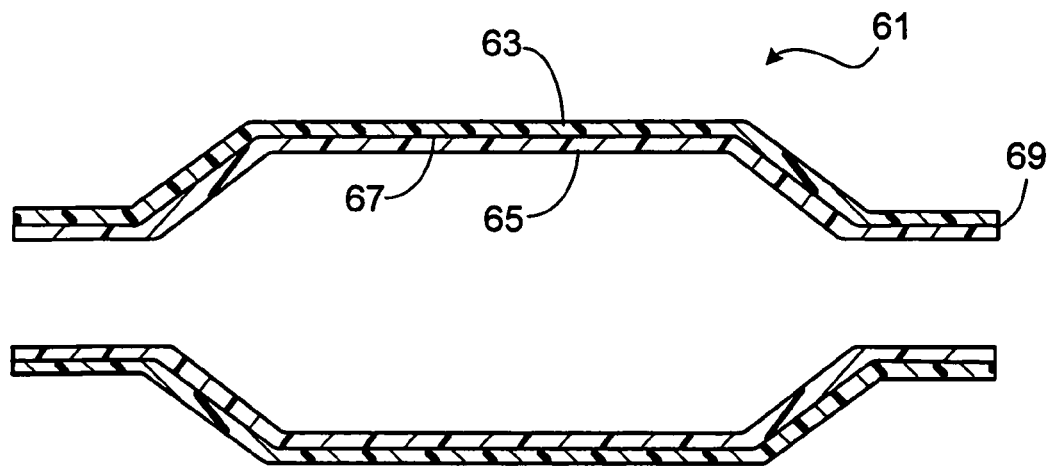
FIG. 4A is a longitudinal cross-sectional view a coextruded balloon, illustrating the balloon wall prior to modification.
Figure 4B:
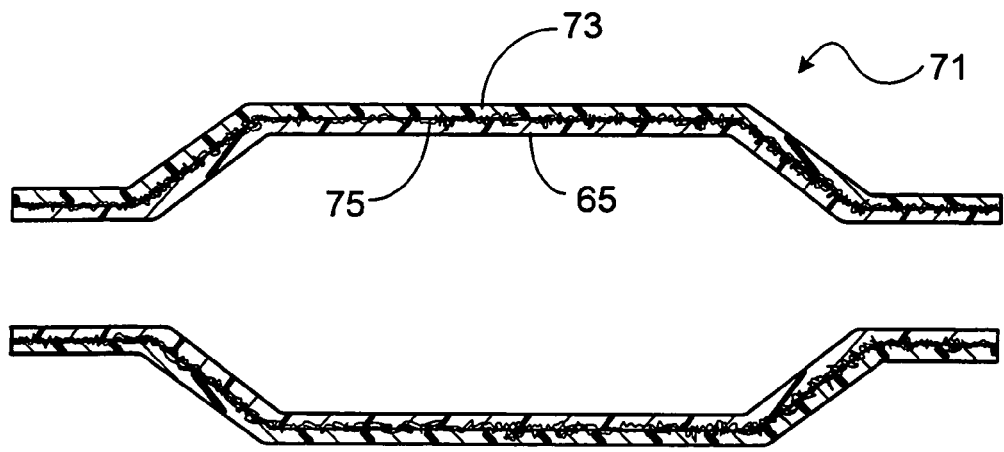
FIG. 4B is a longitudinal cross-sectional view of the coextruded balloon of FIG. 4A, illustrating balloon wall after modification.

Referring to FIGS. 4A and 4B, in a particular embodiment, the base polymer system is formed by coextruding multiple polymer layers of the same or different polymer. A balloon 61 includes a wall 69 that has a first polymer layer 63 and a second polymer layer 65 that are bonded at an interface 67. Balloon 61 can be modified using PIII to provide a modified balloon 71. In the embodiment shown in FIG. 4B, the first layer 63 and interface 67 of balloon 61 is modified with PIII to produce modified layer 73 and modified interface 75 of balloon 71. In this particular embodiment, layer 65 is substantially unmodified. Modification of the first layer 63 of balloon 61 provides a hard, pinhole resistant layer, while modification across the interface enhances adhesion between the adjacent layers in balloon 71. In embodiments such as this, tie layers can be reduced or avoided. In particular embodiments, the balloon can have three or more layers, e.g., five, seven or more layers, e.g., with all or just some of the layers being modified. Balloons formed of coextruded polymer layers are described in Wang, U.S. Pat. Nos. 5,366,442 and 5,195,969, Hamlin, U.S. Pat. No. 5,270,086, and Chin, U.S. Pat. No. 6,951,675, the entire contents of each of which is hereby incorporated by reference herein. The balloon can used, e.g., to deliver a stent. The stent can be a stent such as a bioerodible stent that has been treated using PIII. Suitable stents are described in "BIOERODIBLE ENDOPROSTHESES AND METHODS OF MAKING THE SAME", filed concurrently herewith and assigned U.S. patent application Ser. No. 11/355,368, the entire disclosure of which is hereby incorporated by reference herein.

Figure 5B:
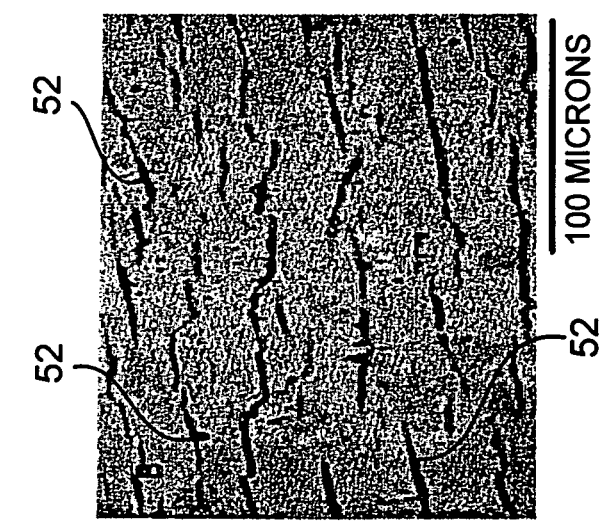
FIG. 5B is a photomicrograph of a balloon surface after modification.
Figure 5A:
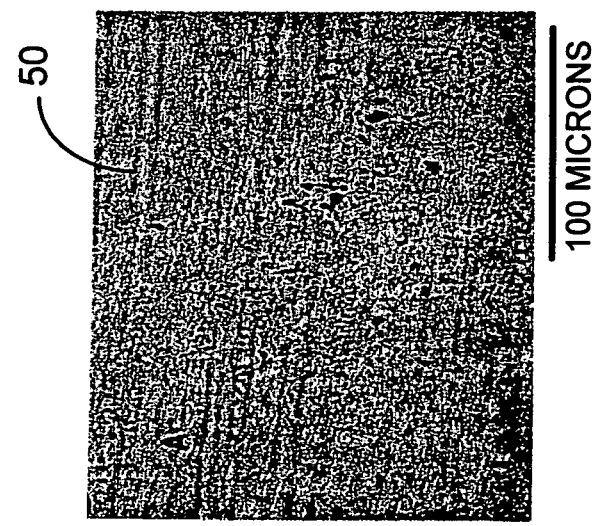
FIG. 5A is a photomicrograph a balloon surface prior to modification.
Figure 5C:
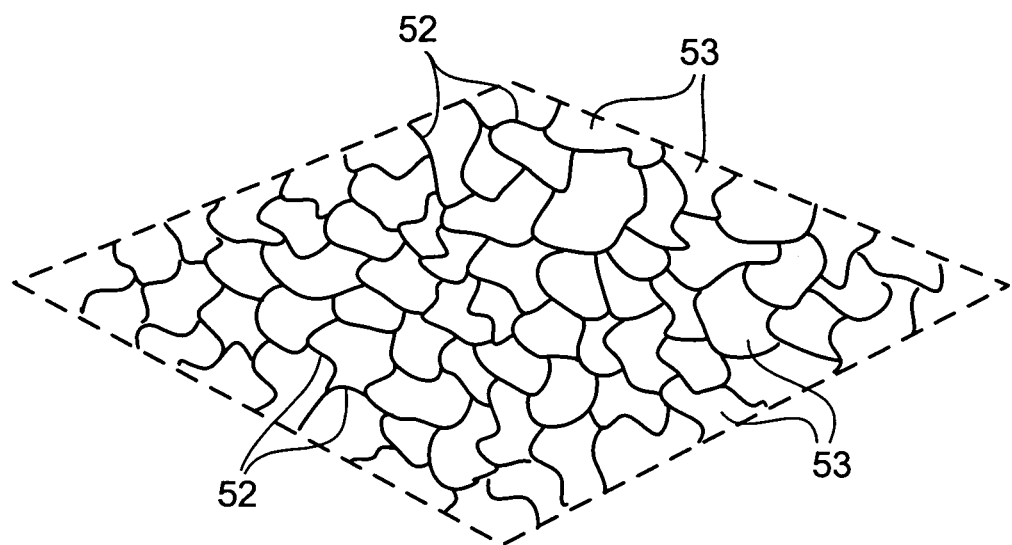
FIG. 5C is a schematic top view of a balloon surface after modification, showing fissures and "islands" that are defined by the fissures.

A balloon can also be modified to provide a desirable surface morphology. Referring to FIG. 5A, a balloon surface 50 prior to modification is illustrated to include a relatively flat and featureless polymer profile (balloon is formed from PEBAX® 7033). Referring to FIG. 5B, after modification by PIII, the surface includes a plurality of fissures 52. The size and density of the fissures can affect surface roughness, which can enhance the friction between the stent and balloon, improving retention of the stent during delivery into the body. Referring to FIG. 5C, in some embodiments, the fracture density is such that non-fractured "islands" 53 of surface defined by fracture lines 52 are not more than about 20 $\mu m^2$, e.g., not more than about 10 $\mu m^2$, or not more than about 5 $\mu m^2$. In embodiments, the fracture lines are, e.g., less 10 µm wide, e.g., less than 5 µm, less than 2.5 µm, less than 1 µm, less than 0.5 µm, or even less than 0.1 µm wide. The fissures or fracture lines can also be utilized as a reservoir for a therapeutic agent, such as an anti-thrombogenic agent, an anesthetic agent or an anti-inflammatory agent. A suitable agent is paclitaxel. The agent can be applied to the balloon surface by soaking or dipping. Other agents are described in U.S. Published Patent Application No. 2005/0216074, the entire disclosure of which is hereby incorporated by reference herein. The balloon can be coated with a protective or release layer such as a salt, sugar or sugar derivative. Suitable layers are described in U.S. Pat. No. 6,939,320, the entire disclosure of which is hereby incorporated by reference herein.

Further embodiments are in the following examples.

EXAMPLES

Materials

Tests are conducted on 2 and 4 mm diameter balloons of PEBAX® 7033, having a Shore D hardness of 69, are manufactured by Boston Scientific, Natick, Mass. Before PIII treatment, the balloons are cleaned with alcohol. Tests are also conducted on 20×20×1 mm PEBAX® 7033 plates which are made by pressing PEBAX® 7033 pellets between polished PTFE plates at 250-300° C. for several minutes. Low-density polyethylene (LDPE) films having a thickness of 50 mkm are used as purchased, as are silicon plates having a thickness of 1 mm.

Methods and Equipment

The large chamber of Rossendorf Research Center is used for PIII (see, e.g., Guenzel, *Surface & Coatings Technology*, 136, 47-50, 2001, or Guenzel, *J. Vacuum Science & Tech. B*, 17(2), 895-899, 1999, the entire disclosure of each of which is hereby incorporated by reference herein). The pressure of residual air is $10^{-3}$ Pa and the working pressure of nitrogen during PIII is $10^{-1}$ Pa. Plasma is generated by a radio frequency generator operating at 13.56 MHz. High voltage pulses of 5 µs duration and 30, 20, 10 and 5 kV peak voltages is used. Pulse repetition frequency from 0.2 Hz to 200 Hz is used to prevent overheating. The PIII treatment of the samples are carried out with doses ranging from $5 \cdot 10^{14}$ to $10^{17}$ ions/cm². The position of the balloons are fixed using a sample holder. Balloons are turned three times (120 degrees each time) during treatment so as to homogeneously treat the outer surface of the balloons. An additional electrode in the form of a metal grid is mounted on the top of the sample holder to prevent direct contact of the samples with rf-plasma between high voltage pulses and to prevent charging of the polymeric material. FTIR ATR spectra can be recorded on either a Nicolet 230 with a diamond ATR crystal or on a Nicolet Magna 750 with a Ge ATR crystal. The number of scans is 100 and resolution is 2 $cm^{-1}$. The spectra are analyzed with Nicolet OMNIC software. UV transmission spectra can be recorded with a 10 nm step in 200-700 nm wavelength spectral region. The optical density scale is used for quantitative analysis to determine the homogeneity of the dose distribution along the polymer surface. The regime of spectral mapping on xy-coordinates is used for analysis of dose distribution homogeneity on a polymer surface. The space resolution at the mapping is approximately 4×4 mm. Micro-Raman spectra are recorded in backscattering mode, excited by Nd:YAG laser irradiation (2ω, λ=532.14 nm), on a Jobin Yvon HR800 with LabRam analysis software. An optical microscope is used for focusing of the laser beam and for collection of the Raman scattered light. The intensity of laser beam is controlled to prevent overheating of the samples. Spectral resolution is 4 $cm^{-1}$. The number of scans acquired is between 100 and 4000, the actual number depending upon the signal-to-noise for the sample.

Tensile tests are performed on a Zwick tensile machine. PEBAX® 7033 strips of 30×2×0.03 mm are used. For strips, the balloons are cut using multi-blade knife including six blades joined together through 2 mm plates. The ends of the strips are bonded to aluminum foil using epoxy glue for strong mechanical fixing to the clamps. Five strips are used for one sample analysis. Load direction of the test corresponds to the longitudinal axis of the balloon. A crosshead speed of 5 mm/min is applied. The analysis of the results is done by strain-stress diagram. Modulus, elongation and stress at breaking are analyzed. Modulus is determined by the beginning of the linear part of strain-stress curve.

Scratch tests are performed with a tester that includes a table having a fixed sample and a balance with a diamond indenter having a tip that is 1 micron. The table moves with a speed of 0.15 mm/sec. The diamond indenter can be loaded with 1, 2, 5, 10, 20 and 50 grams of weight. Plates of PEBAX® 7033 are used for the scratch test. The depth and width of the scratch is determined by optical profilometry. The scratch tester is calibrated on polyethylene, polyamide and polytetrafluorethylene plates. Hardness is determined by the AFM method in contact mode using a silicon tip having a 20 nm diameter and a cantilever with a constant of 80 nN/nm (see, e.g., Prikryl, *Surface & Coatings Technology*, 200, 468-471, 2005, the entire disclosure of which is hereby incorporated by reference herein).

Structural Changes in PEBAX® 7033 Samples after Treatment with PIII

Figure 6:
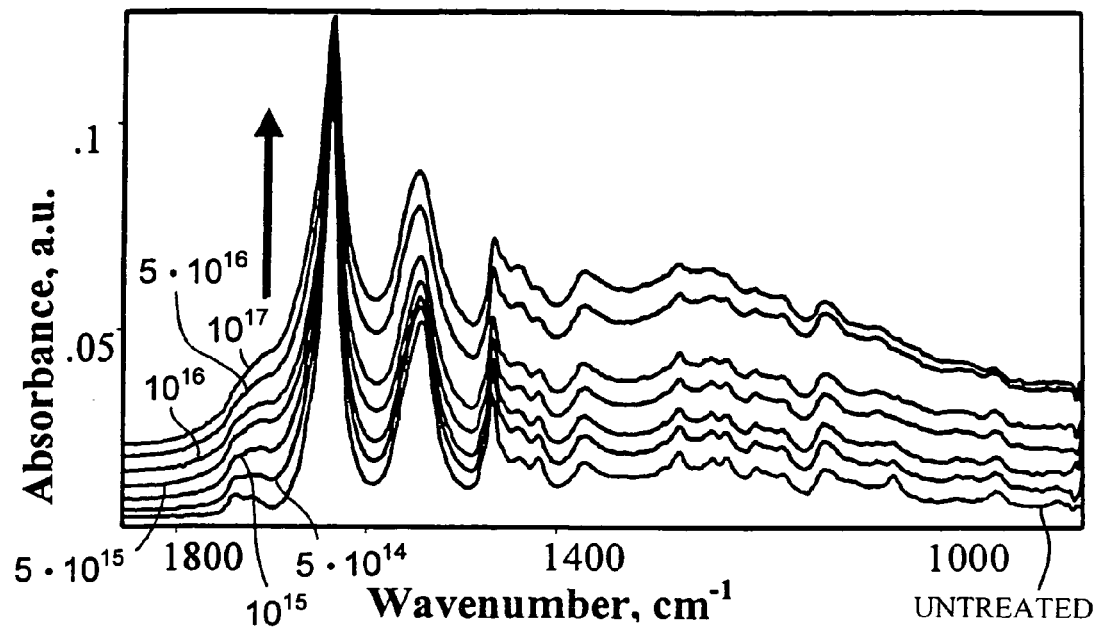
FIG. 6 is a series of FTIR ATR spectra of PEBAX® 7033 films taken from 1850 $cm^{-1}$ to 900 $cm^{-1}$ after PIII treatment at 30 keV; the bottom spectrum being the untreated film, the other spectra being films treated respectively with $5\times10^{14}$, $10^{15}$, $5\times10^{15}$, $10^{16}$, $5\times10^{16}$ and $10^{17}$ ions/$cm^2$.

FIG. 6 is a series of FTIR ATR spectra of PEBAX® 7033 films taken from 1850 $cm^{-1}$ to 900 $cm^{-1}$ after PIII treatment at 30 keV. The bottom spectrum is the untreated film, and the other spectra are films treated respectively with $5 \times 10^{14}$, $10^{15}$, $5 \times 10^{15}$, $10^{16}$, $5 \times 10^{16}$ and $10^{17}$ ions/cm². A broadening of 1638 $cm^{-1}$ peak and the appearance of a doublet at 1720/1737 $cm^{-1}$ with PIII dose is believed caused by new, overlapping lines in the regions of 1650-1750 $cm^{-1}$. These new lines are vibrations of carbon-carbon double bonds and carbon-oxygen double bonds. The appearance of such lines is connected with the carbonization and oxidation the PEBAX® polymer under the ion source.

Figure 7:
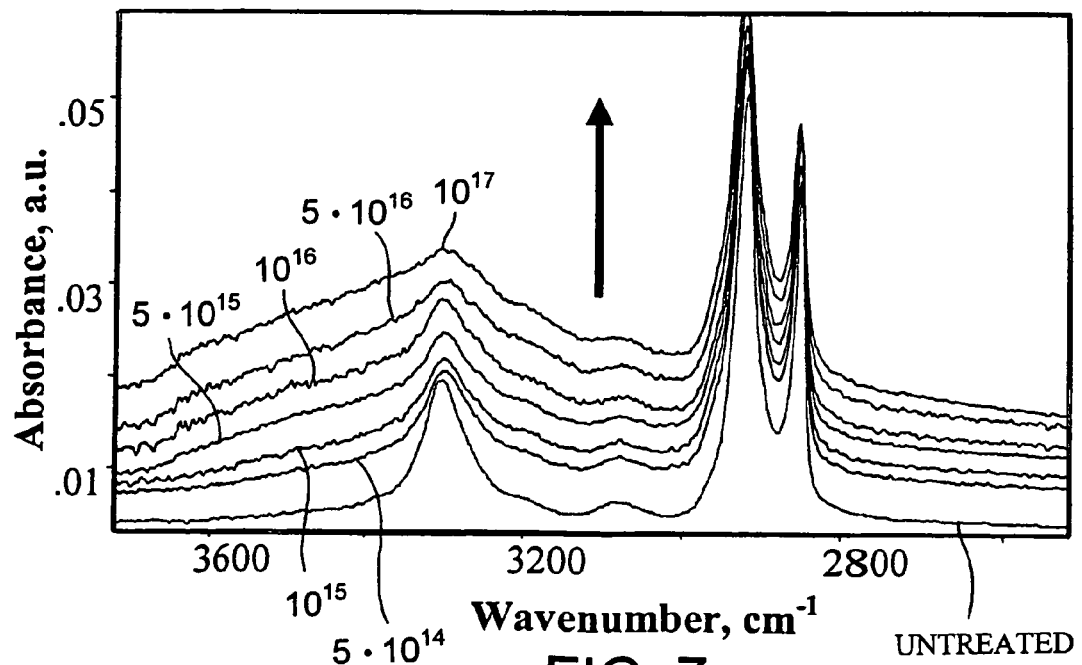
FIG. 7 is a series of FTIR ATR spectra of PEBAX® 7033 films taken from 3700 $cm^{-1}$ to 2550 $cm^{-1}$ after PIII treatment at 30 keV; the bottom spectrum being the untreated film, the other spectra being films treated respectively with $5\times10^{14}$, $10^{15}$, $5\times10^{15}$, $10^{16}$, $5\times10^{16}$ and $10^{17}$ ions/$cm^2$.

FIG. 7 is a series of FTIR ATR spectra of PEBAX® 7033 films taken from 3700 $cm^{-1}$ to 2550 $cm^{-1}$ after PIII treatment at 30 keV. The bottom spectrum is the untreated film, and the other spectra are films treated respectively with $5 \times 10^{14}$, $10^{15}$, $5 \times 10^{15}$, $10^{16}$, $5 \times 10^{16}$ and $10^{17}$ ions/cm². A new line at 3600-3200 cm$^{-1}$ region is observed in spectra. This broad peak corresponds to O—H vibrations of hydroxyl groups. While O—H groups exist in the untreated macromolecules of PEBAX® (at chain ends), their concentration is much lower than after PIII treatment. The appearance of intensive O—H lines in the spectra of the treated samples results from depolymerization processes in which broken polymer chain ends react with oxygen, effectively increasing the O—H concentration in the sample.

Figure 8:
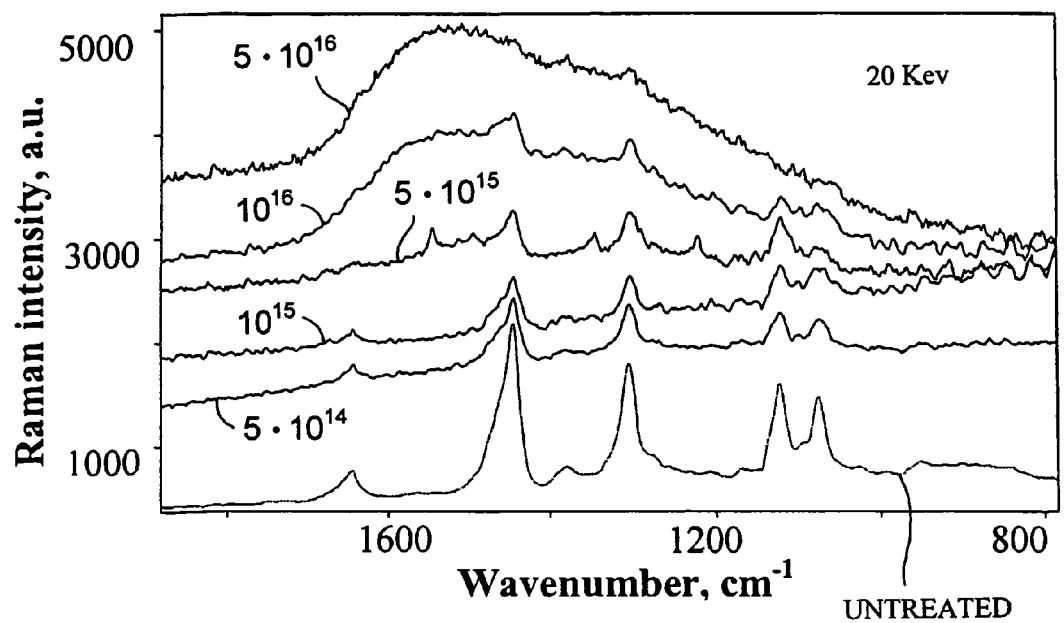
FIG. 8 is a series of Raman spectra of PEBAX® 7033 films taken from 1900 $cm^{-1}$ to 775 $cm^{-1}$ after PIII treatment at 20 keV; the bottom spectrum being the untreated film, the other spectra being films treated respectively with $5\times10^{14}$, $10^{15}$, $5\times10^{15}$, $10^{16}$ and $5\times10^{16}$ ions/$cm^2$.

FIG. 8 is a series of Raman spectra of PEBAX® 7033 films taken from 1900 cm$^{-1}$ to 775 cm$^{-1}$ after PIII treatment at 20 keV. The bottom spectrum is the untreated film, and the other spectra are films treated respectively with $5\times10^{14}$, $10^{15}$, $5\times10^{15}$, $10^{16}$ and $5\times10^{16}$ ions/cm$^2$. In the spectrum of the untreated PEBAX®, a lines at 1645, 1446, 1381, 1305, 1121, 1074 cm$^{-1}$ corresponded to the vibrations of polyamide-polyether macromolecule (PEBAX®). In spectra of treated samples, the intensity of such lines decreases with increasing PIII dose, and a new wide peak centered at 1510 cm$^{-1}$ appears. This peak corresponds to vibrations of amorphous carbon. At high doses, the vibrations associated with the PEBAX® essentially disappear and are replaced by the broad peak associated with amorphous diamond. These strong changes in the Raman spectra is observed only in outer portions of the film, indicating that only outer portions of the film are carbonized. Defocusing, or shifting laser focus to deeper portions of the film gives the spectrum of untreated PEBAX®.

Figure 9:
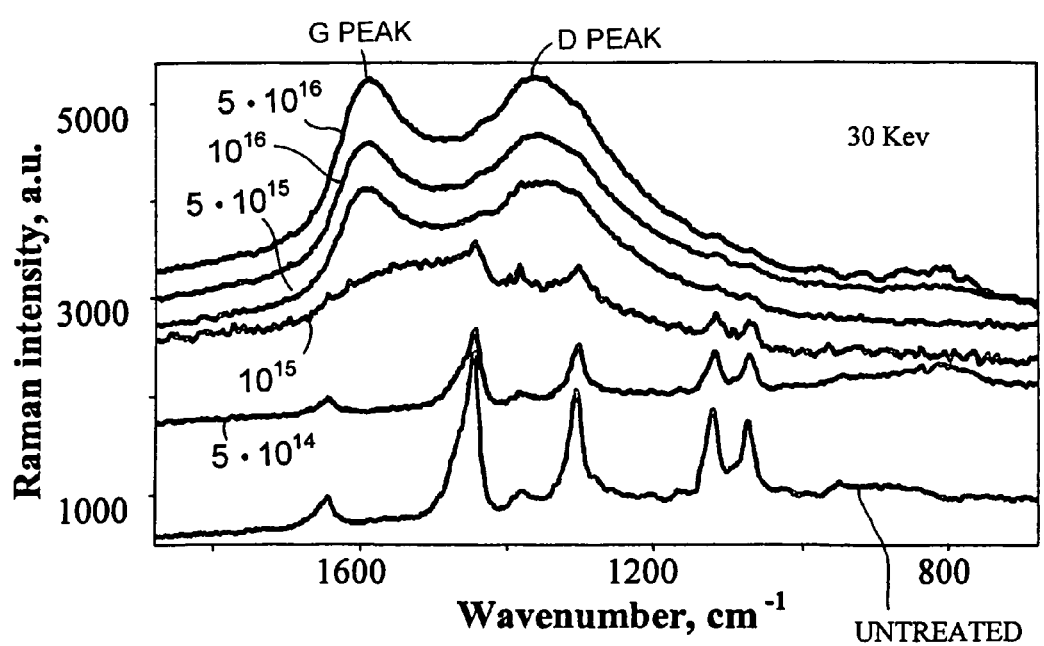
FIG. 9 is a series of Raman spectra of PEBAX® 7033 films taken from 1900 $cm^{-1}$ to 775 $cm^{-1}$ after PIII treatment at 30 keV; the bottom spectrum being the untreated film, the other spectra being films treated respectively with $5\times10^{14}$, $10^{15}$, $5\times10^{15}$, $10^{16}$, $5\times10^{16}$ and $10^{17}$ ions/$cm^2$.

FIG. 9 is a series of Raman spectra of PEBAX® 7033 films taken from 1900 cm$^{-1}$, to 775 cm$^{-1}$ after PIII treatment at 30 keV. The bottom spectrum is the untreated film, and the other spectra are films treated respectively with $5\times10^{14}$, $10^{15}$, $5\times10^{15}$, $10^{16}$, $5\times10^{16}$ and $10^{17}$ ions/cm$^2$. After PIII treatment with 30 keV energy, the Raman spectra of the samples treated at relatively low doses ($5\times10^{14}$-$1\times10^{15}$ ions/cm$^2$) appear to be very similar to those shown in FIG. 8. However, at relatively high doses ($5\times10^{15}$ and above), the Raman spectra contain two relatively sharp peaks at 1580 and 1350 cm$^{-1}$. These lines correspond to carbon in the form of graphitic structures and DLC structures. The peak at 1580 cm$^{-1}$ is called the G-peak and the peak at 1350 cm$^{-1}$ is called the D-peak. These lines are observed only in samples treated by ions with energy of 30 keV and at higher doses Raman spectra of diamond-like carbon materials are described by Shiao, *Thin Solid Films*, v. 283, 145-150 (1996), the entire disclosure of which is hereby incorporated by reference herein.

Figure 10B:
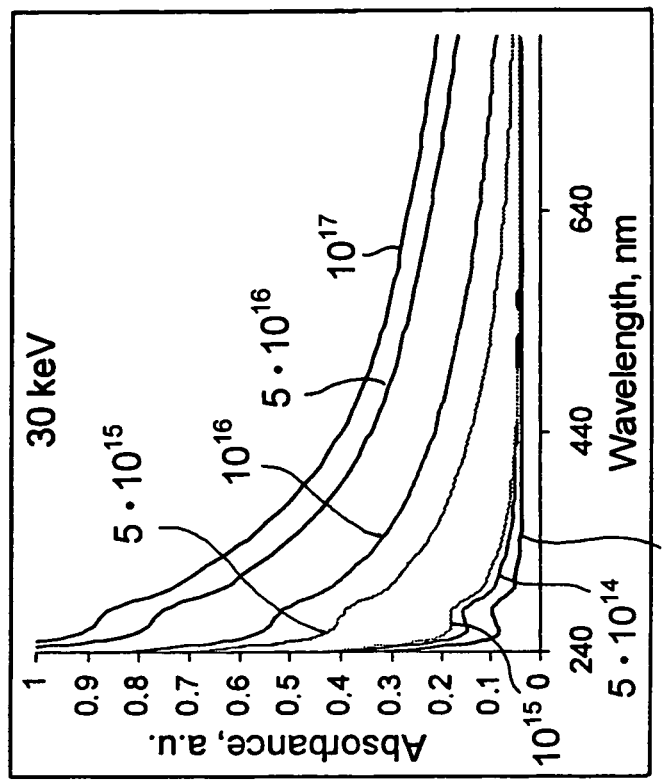
FIG. 10B is a series of UV-Vis transmission spectra of PEBAX® 7033 films taken from 500 nm to 240 nm after PIII treatment at 30 keV; the bottom spectrum being the untreated film, the other spectra being films treated respectively with $5\times10^{14}$, $10^{15}$, $5\times10^{15}$, $10^{16}$, $5\times10^{16}$ and $10^{17}$ ions/$cm^2$.
Figure 10A:
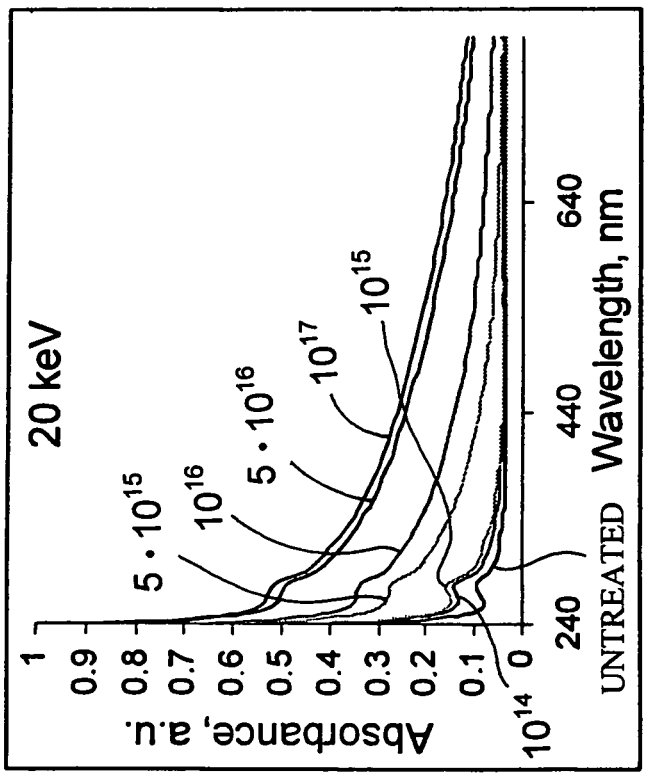
FIG. 10A is a series of UV-Vis transmission spectra of PEBAX® 7033 films taken from 500 nm to 240 nm after PIII treatment at 20 keV; the bottom spectrum being the untreated film, the other spectra being films treated respectively with $5\times10^{14}$, $10^{15}$, $5\times10^{15}$, $10^{16}$, $5\times10^{16}$ and $10^{17}$ ions/$cm^2$.

Referring to FIGS. 10A and 10B, the structural transformations in PEBAX® under PIII can also be observed by transmission spectra in the ultraviolet and visual region. FIG. 10A is a series of UV-Vis transmission spectra of PEBAX® films taken from 500 nm to 240 nm after PIII treatment at 20 keV, while FIG. 10 B is a series after treatment at 30 keV. In both figures, the bottom spectrum is the untreated film, and the other spectra are films treated respectively with $5\times10^{14}$, $10^{15}$, $5\times10^{15}$, $10^{16}$, $5\times10^{16}$ and $10^{17}$ ions/cm$^2$. PIII modification leads to a formation of additional overlapping lines in the spectra. From the spectra, it is apparent that the short wavelength lines have a stronger intensity than long wavelength lines and that the intensity of absorption increases with increasing dose. These additional lines are attributed to absorption of light by π-electrons in unsaturated carbon-carbon structures, including condensed aromatic and polyene structures. An increase in the number of condensed structures shifts the position of the absorbing lines to red side of the spectrum, indicating the formation of long conjugated unsaturated carbon-carbon groups.

Figure 11B:
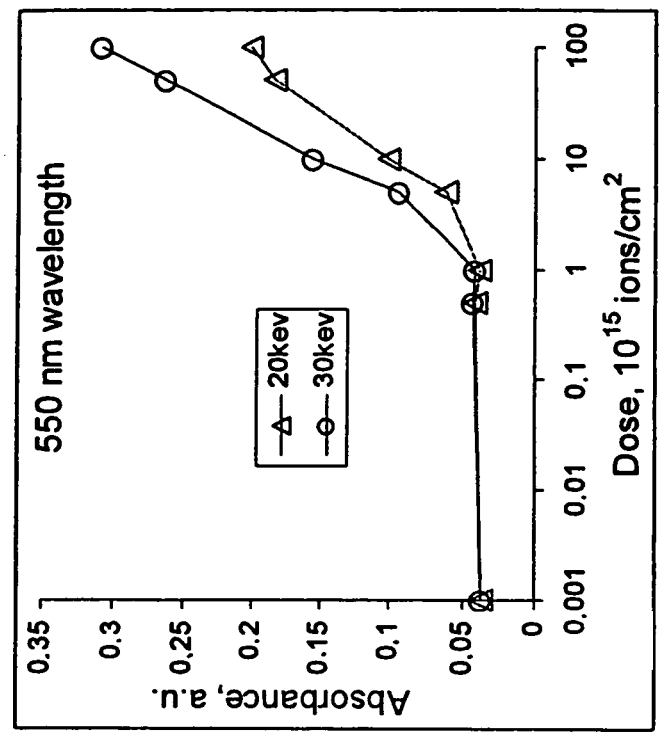
FIG. 11B shows optical density of PEBAX® 7033 films at 550 nm as a function PIII dose at 20 keV and 30 keV.
Figure 11A:
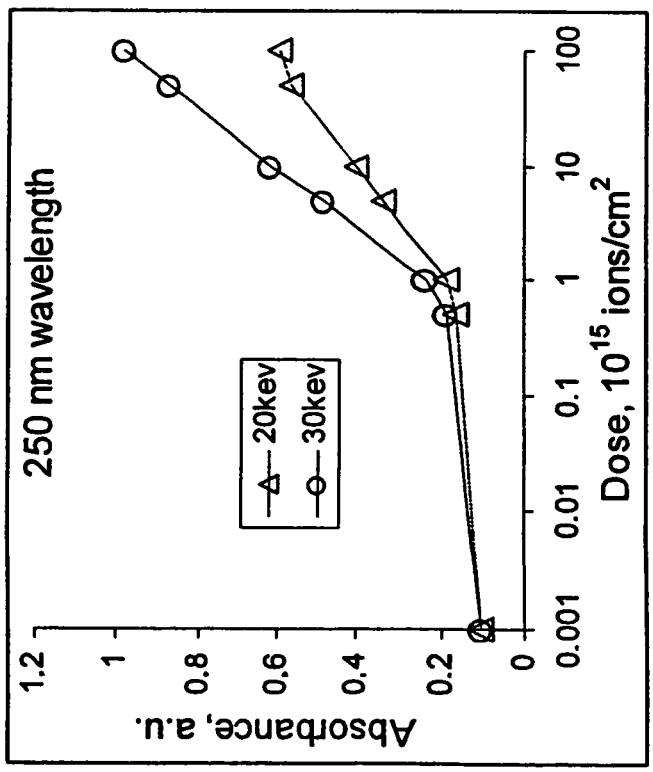
FIG. 11A shows optical density of PEBAX® 7033 films at 250 nm as a function PIII dose at 20 keV and 30 keV.

Referring to FIGS. 11A and 11B, quantitative analysis of the unsaturated carbon-carbon structures in PEBAX® 7033 films is done by optical density at two separate wavelengths. In such an analysis, 250 nm corresponds to n=1 and 550 nm corresponds to n=4, where n is number of conjugated aromatic structures. At low dose, the rate of unsaturated carbon-carbon structures collection is low. However, a strong increase in absorption starts from a dose of about $10^{15}$ ions/cm$^2$. The formation of n=1 structures starts at lower dose, and the highly conjugated carbon-carbon structures with n=4 appears at higher dose.

Figure 12:
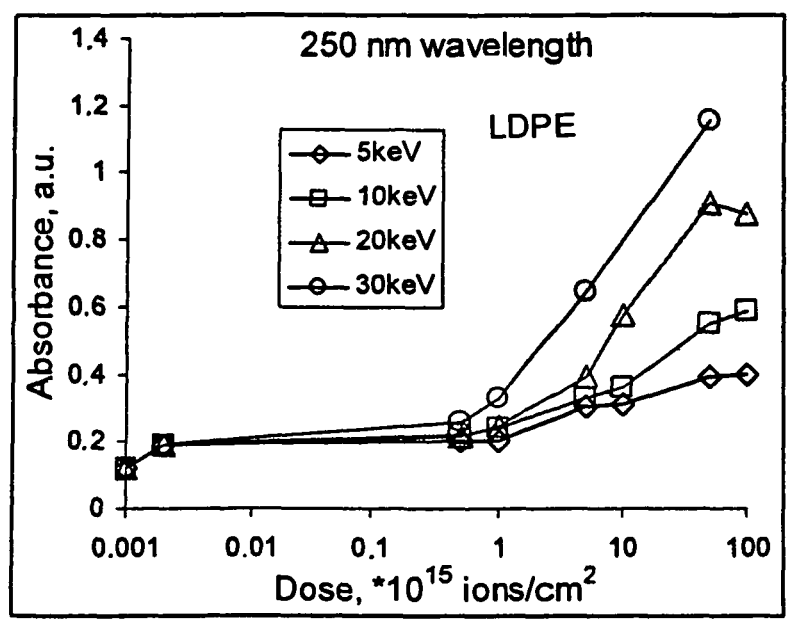
FIG. 12 shows optical density of low-density polyethylene (LDPE) films at 250 nm as a function PIII dose at 5 keV, 10 keV, 20 keV and 30 keV.

Referring now to FIG. 12, when comparing the UV spectra of PEBAX® 7033 films and those of LDPE, the PEBAX® films have a lesser level of unsaturated carbon-carbon structures. Because transmission spectra do not contain absorption lines for initial films of PEBAX® films and LDPE, the optical density at 250 nm can be interpreted as absorption only from the modified polymer region. Therefore, the value of the optical density at the same dose of PIII can be used for quantitative comparison. The estimation of unsaturated carbon-carbon structures in PEBAX® films gives 68±8% in comparison with LDPE for all doses of PIII. This number means that approximately two-thirds of the PEBAX® takes part in formation of carbonized layer.

Figure 13:
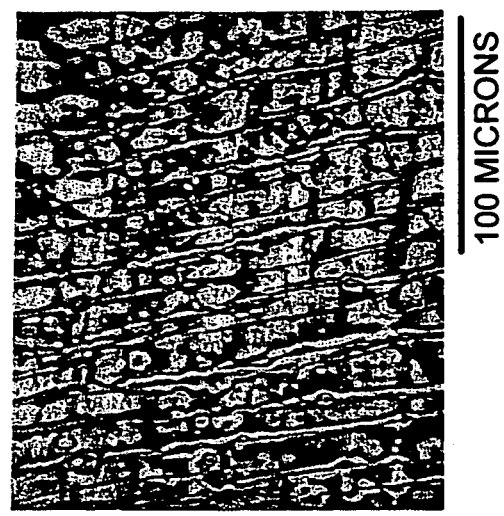
FIG. 13 is a photomicrograph a PEBAX® 7033 balloon surface after treatment with $10^{16}$ ions/$cm^2$ at 30 keV.

Referring to FIG. 13, the surface morphology of the PEBAX® 7033 films change strongly at high dose of PIII treatment, which is observable in photomicrographs. At low doses of treatment, the surface morphology does not significantly change. At dose of $10^{15}$ ions/cm$^2$, the surface contains some cracks and fissures. However, at higher doses, an extensive network of cracks and fissures is observed. Despite the crack and fissure network, peeling of the carbonized region from the bulk polymer is not observed.

Mechanical Properties of PEBAX® Films after Treatment with PIII

Figure 14:
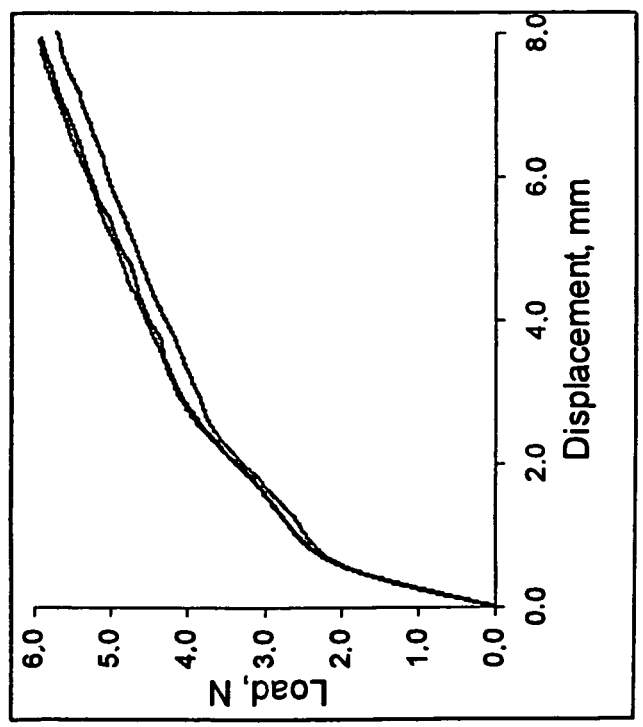
FIG. 14 shows stress-stain curves for several PEBAX® 7033 films treated with PIII.

Referring to FIG. 14, stress-strain curves of PIII treated PEBAX® 7033 films are nearly identical to the corresponding stress-strain curves of untreated films. The curves of all PEBAX® films tested are similar for all dose and energies.

Figure 15:
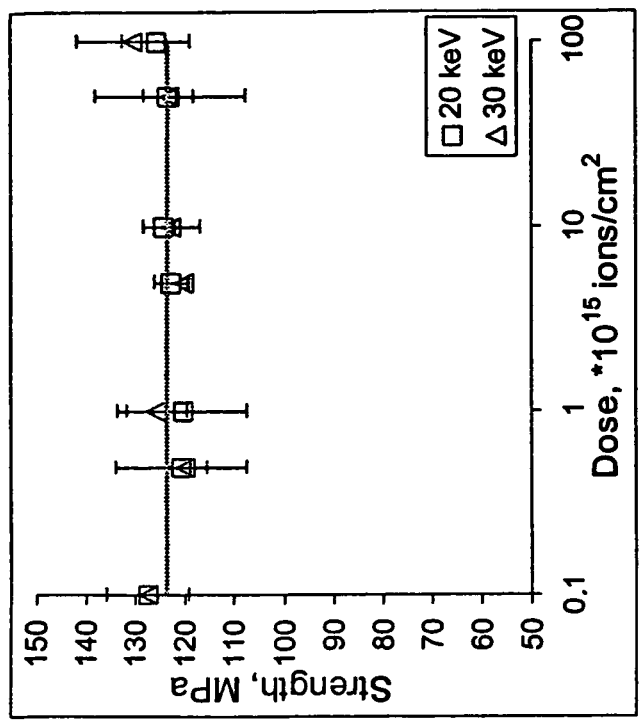
FIG. 15 shows strength of PEBAX® 7033 films treated with PIII as a function of dose at 20 keV and 30 keV.
Figure 17:
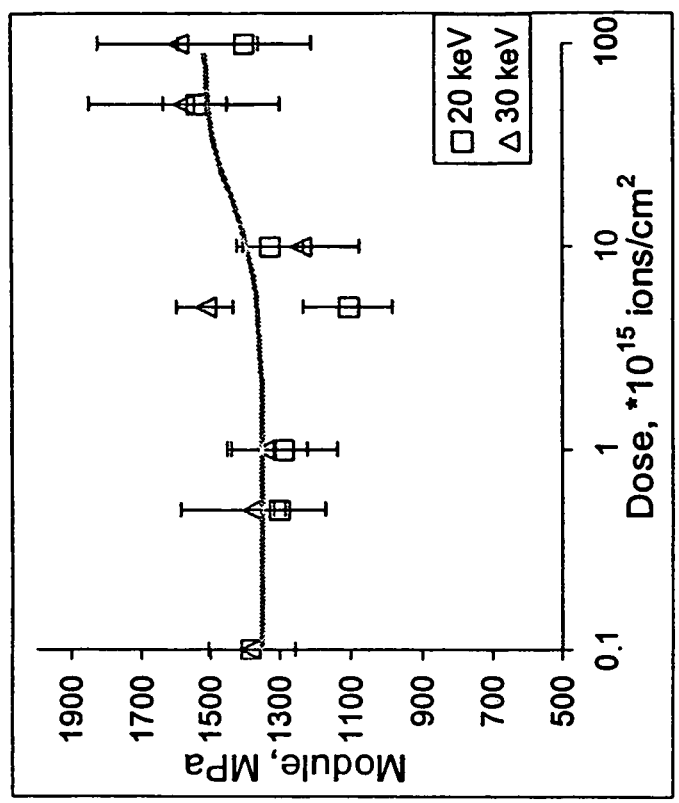
FIG. 17 shows modulus of elasticity of PEBAX® 7033 films as a function of dose at 20 keV and 30 keV.
Figure 16:
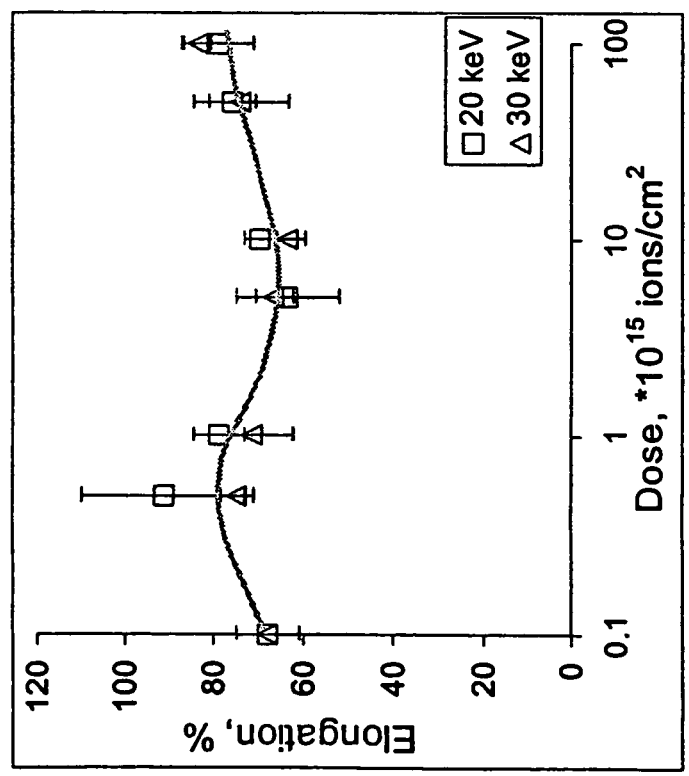
FIG. 16 shows percent elongation at break of PEBAX® 7033 films as a function of dose at 20 keV and 30 keV.

Referring to FIG. 15, strength at breaking also does not appear to change after PIII treatment. In addition, referring to FIGS. 16 and 17, percent elongation at break and modulus of elasticity are statistically unaffected by PIII treatment.

The thickness of the modified region (for these samples estimated at less 100 mm) relative to the thickness of the unmodified region (for these samples estimated at around 30,000 nm) can be used to explain why PIII modification of PEBAX® films does not lead to significant changes in the mechanical properties tested of those films.

Surface Hardness of PEBAX® Films after PIII Treatment and Scratch Testing

Figure 21:
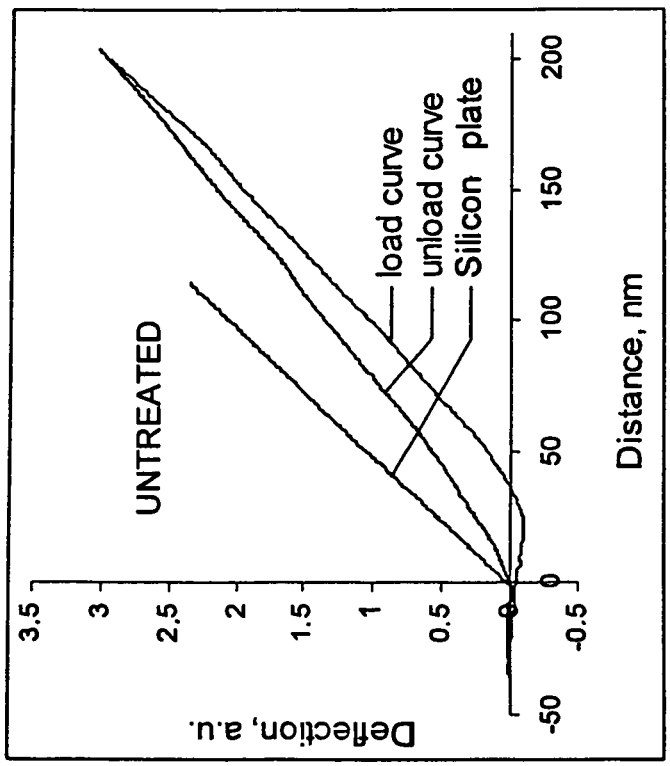
FIG. 21 shows load curves obtained using atomic force microscopy (AFM) for a hard silicon plate (as reference) and an untreated PEBAX® 7033 plate.

Referring to FIG. 21, a load curve for a silicon plate is used as reference, and shows typical deformation behavior of a cantilever on hard surface. The slope of the curve is relatively steep (indicating a high modulus of elasticity) and little or no hysteresis occurs. In contrast, the load curve for untreated PEBAX® 7033 film is not as steep (indicating a low modulus of elasticity) and shows significant hysteresis. Initially, the PEBAX® load curve goes lower, corresponding to deformation of the polymeric material under tip load. The unload curve corresponds to retrace movement of the tip, and since the load and unload curve are not identical, hysteresis is observed. Hysteresis is caused by mechanical energy loss due to movement and conformational transitions of polymer macromolecules under the load. Such behavior is typical of relatively soft materials.

Figure 22:
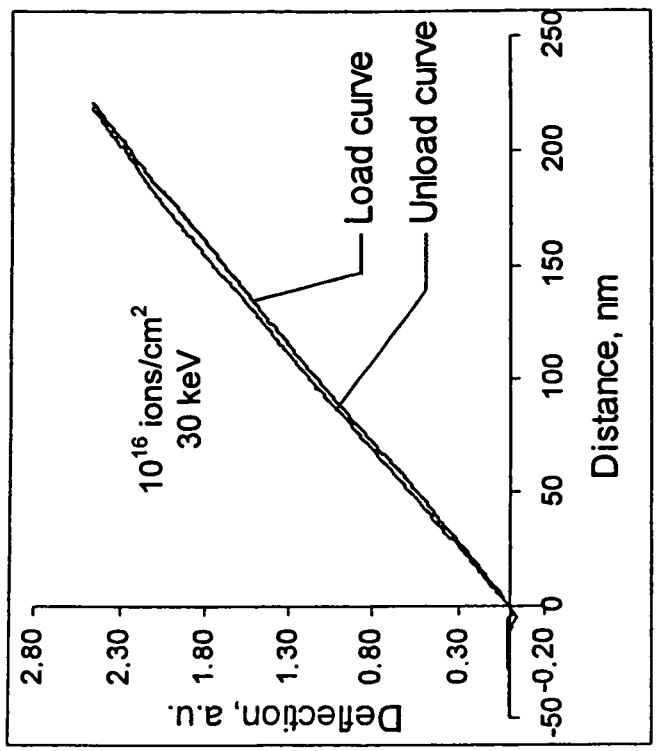
FIG. 22 shows load curves obtained using AFM for a PEBAX® 7033 plate treated with PIII at a dose of $10^{16}$ ions/$cm^2$ and 30 keV.

Referring now to FIG. 22, which is a load curve for a PEBAX® 7033 plate treated with PIII at a dose of $10^{16}$ ions/cm$^2$ and 30 keV. Note that the curve is generally steeper than the untreated plate curve shown in FIG. 21, and the hysteresis has nearly disappeared. Such is curve is similar to the silicon reference curve, and is indicative that the PEBAX® plate has a hard surface.

Figure 24:
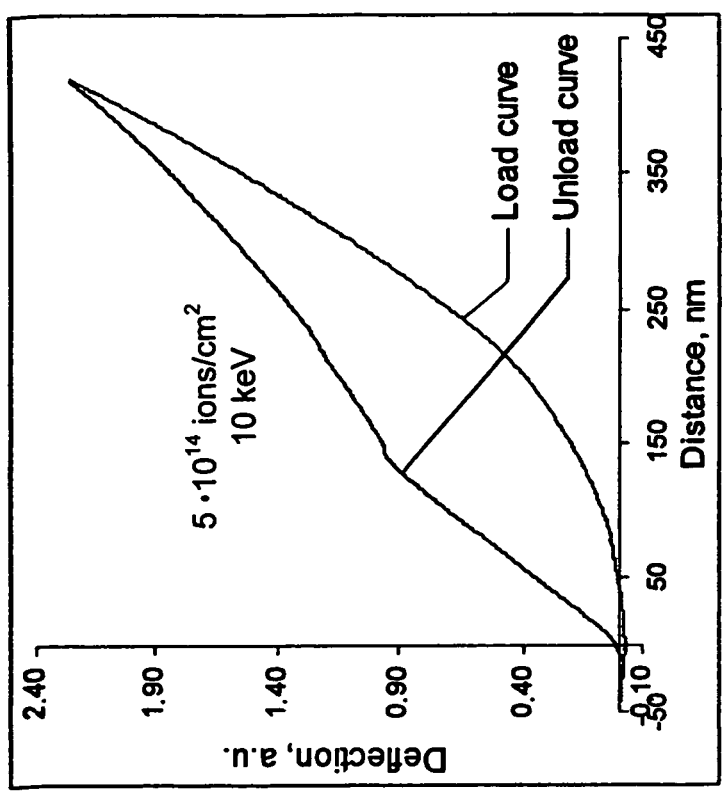
FIG. 24 shows load curves obtained using AFM for a PEBAX® 7033 plate treated with PIII at a dose of $5\times10^{14}$ ions/$cm^2$ and 10 keV.
Figure 23:
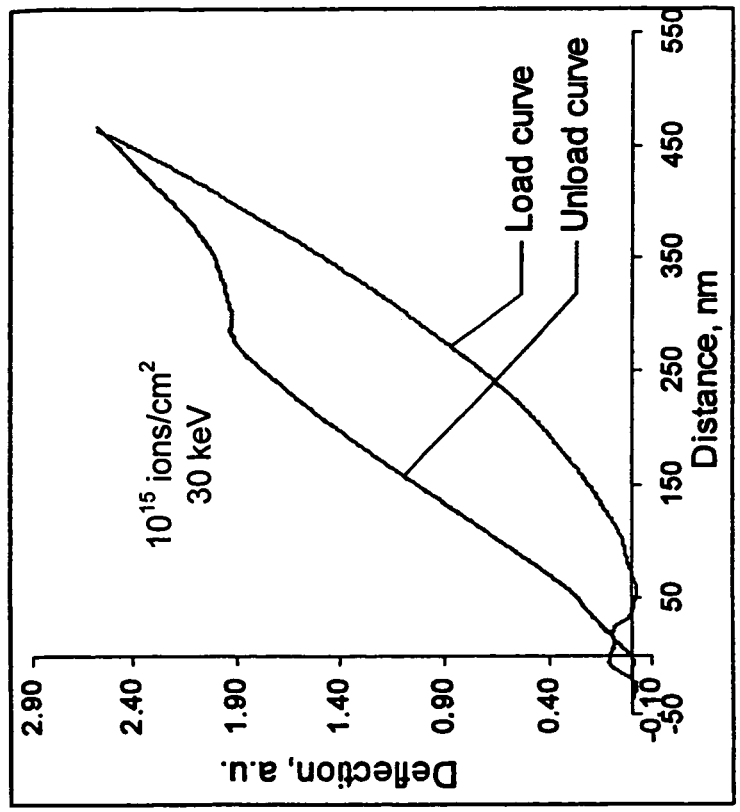
FIG. 23 shows load curves obtained using AFM for a PEBAX® 7033 plate treated with PIII at a dose of $10^{15}$ ions/$cm^2$ and 30 keV.

Referring to FIGS. 23 and 24, at relatively low doses, the load curve for treated PEBAX® plates are more complex. Generally, there are two parts to these load curves. The first part has steep curve, corresponding to a high modulus, while the second part of the curve is not as steep, corresponding to a lower modulus. The observed complex character of the load curve is believed to be caused by penetration of the AFM tip through carbonized region. At relatively low doses, this layer is not hard and thick enough to stop penetration by the tip.

Figure 25:
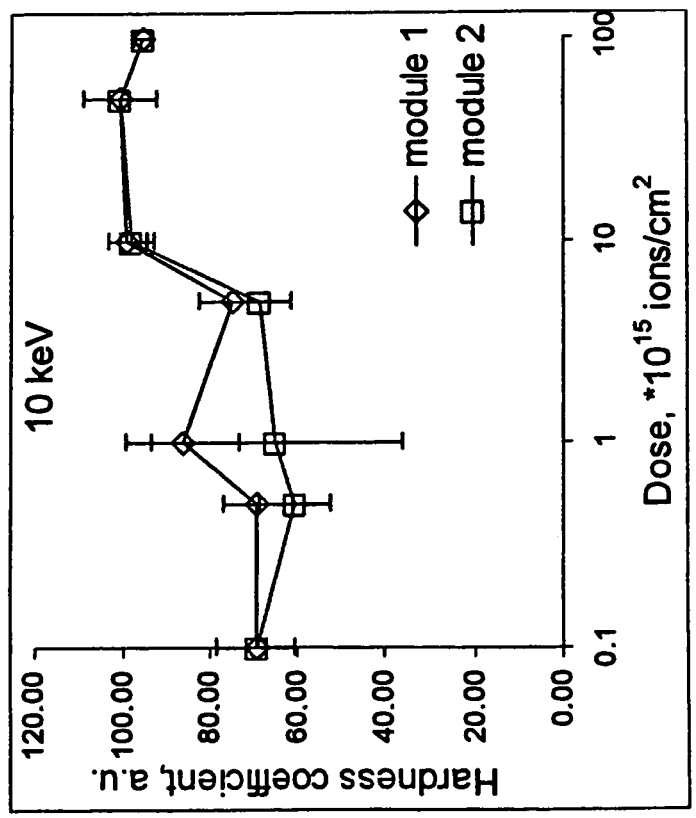
FIG. 25 shows apparent hardness coefficient a first part of a load curve (module 1) and a second part of a load curve (module 2) for PEBAX® 7033 plates treated at various doses at 10 keV.

FIG. 25 shows the dependence of the modulus of elasticity of the two parts of the load curves described above. As can be seen in FIG. 25, the modulus of elasticity of the first part initially grows, while the modulus of elasticity of the second part of the load curve remains relatively constant. However, at a dose of $10^{16}$ ions/cm$^2$, the curve becomes linear and the modulus of elasticity of each part becomes equal. It is believed that at this dose, the carbonized layer becomes hard enough to hold the tip load.

Figure 19:
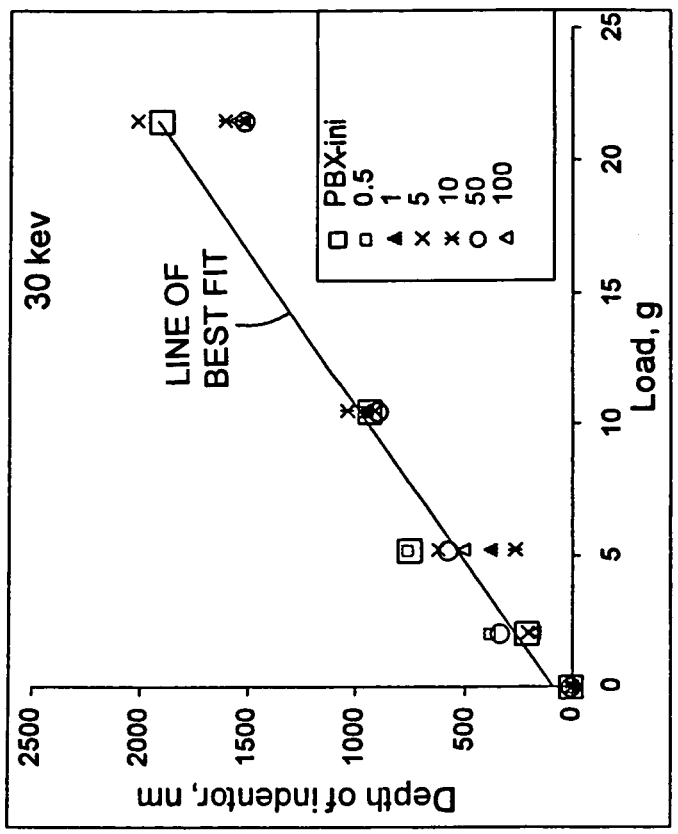
FIG. 19 shows scratch testing of PEBAX® 7033 plates at a variety of doses at 30 keV (dose in box is expressed in multiples of $10^{15}$ ions/$cm^2$).
Figure 18:
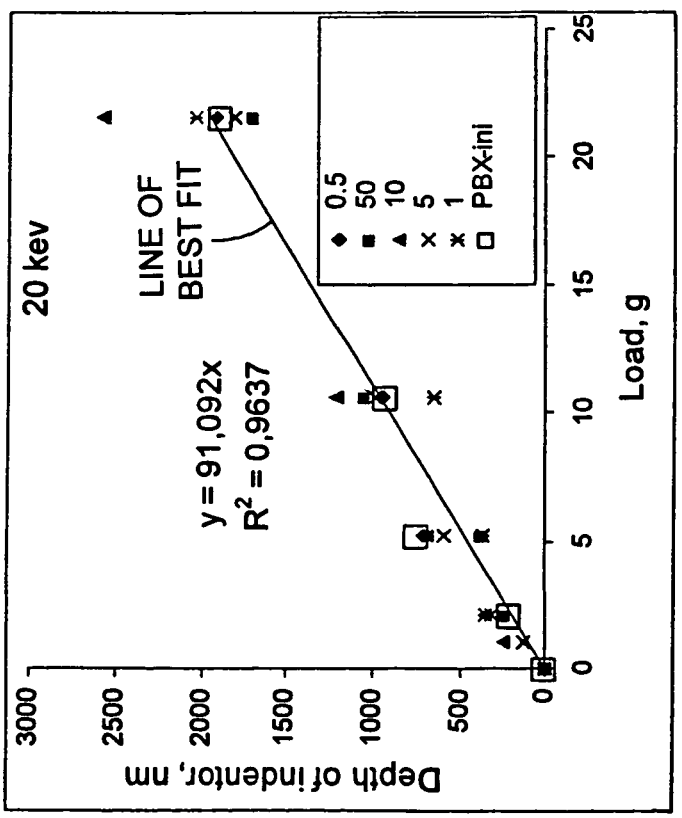
FIG. 18 shows scratch testing of PEBAX® 7033 plates at a variety of doses at 20 keV (dose in box is expressed in multiples of $10^{15}$ ions/$cm^2$).

Referring to FIGS. 18 and 19, the results of scratch tests are shown. Different loads are applied to PEBAX® 7033 plates treated at a variety of doses at 20 keV and 30 keV (dose in box is expressed in multiples of $10^{15}$ ions/cm$^2$). No significant differences are found between the modified and unmodified PEBAX® plates.

Figure 20:
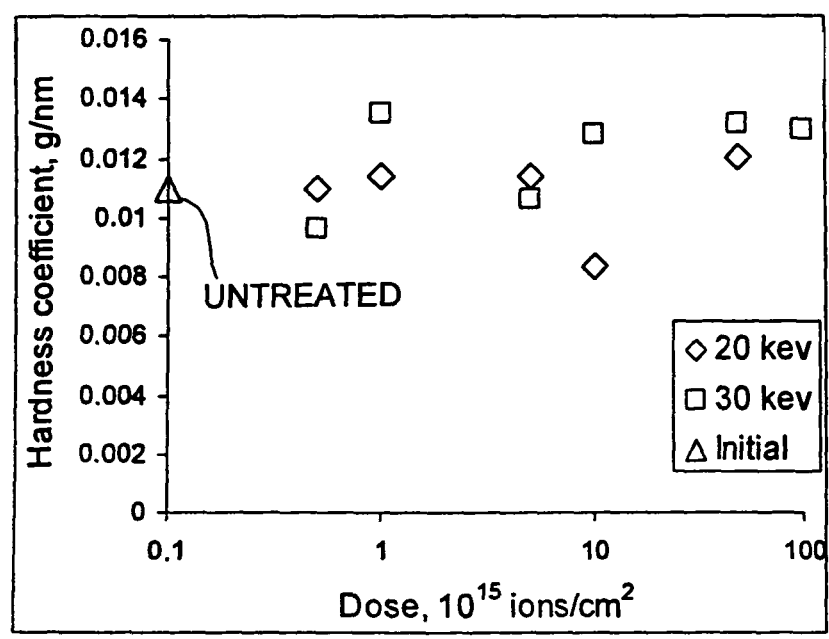
FIG. 20 shows hardness coefficient of PEBAX® 7033 plates as a function of dose at 20 keV and 30 keV.

Referring now to FIG. 20, also no significant differences are found in the hardness coefficient of untreated PEBAX® plates when compared to treated PEBAX® plates at a variety of doses at 20 keV and 30 keV. Since the thickness of the modified region is very small, the scratch tester is not sensitive enough to measure the changes in the modified region. It is believed that the diamond indenter of the scratch tester penetrates through the thin modified region.

Figure 26:
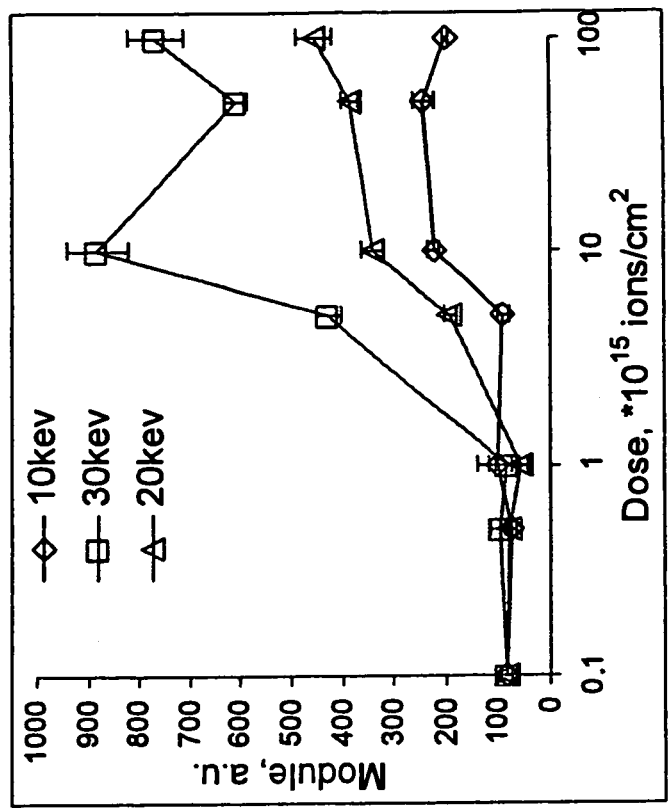
FIG. 26 shows modulus of elasticity of PEBAX® 7033 plates as a function of dose at 10 keV, 20 keV and 30 keV.

Referring to FIG. 26, the modulus of elasticity of the carbonized region depends on the energy of penetrating ions, with higher energies giving a higher modulus. An especially high modulus is observed for an energy of 30 keV. Sharp increase of the modulus after 30 keV can be connected with formation of graphitic and DLC structures.

Homogeneity of Surface Hardness of PEBAX® Films after PIII Treatment

Figure 27:
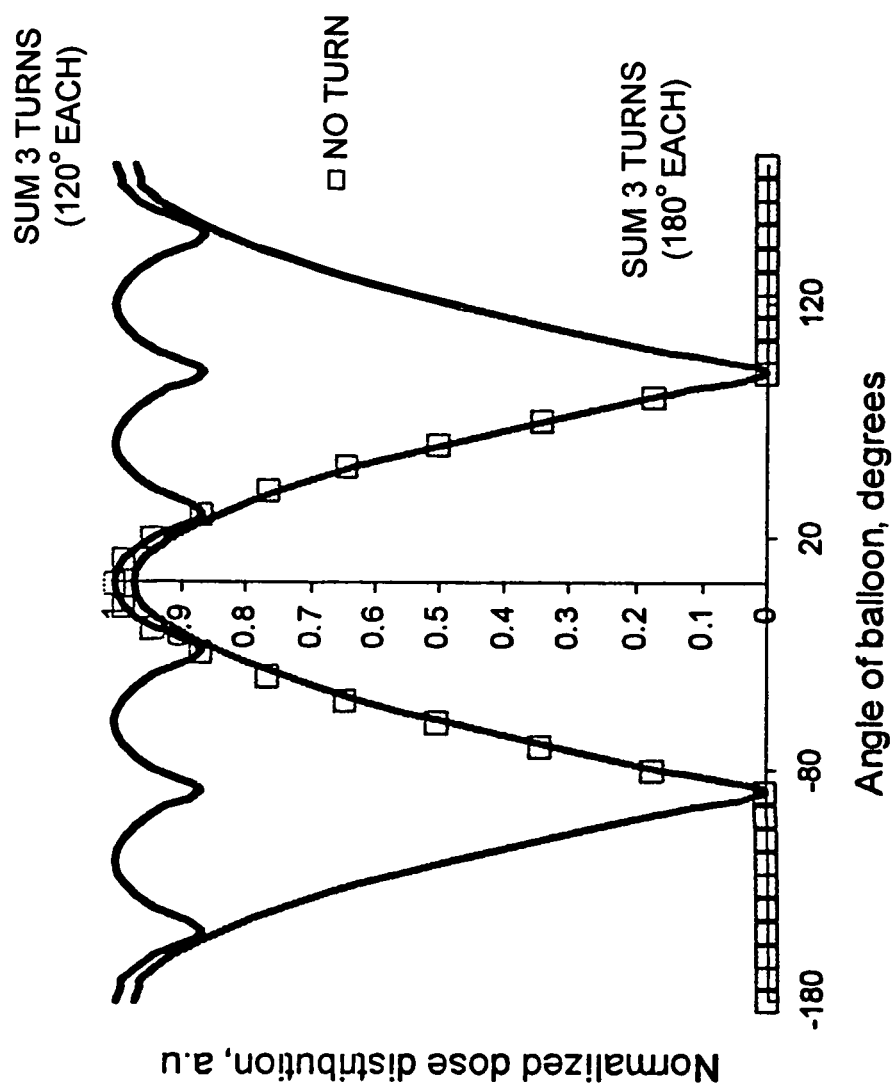
FIG. 27 shows a normalized dose distribution as a function of balloon angle.

As discussed above, the hardness of the modified region is a function of dose and ion energy. For homogeneity of surface hardness, the dose should be distributed equally over an entire surface. Because the balloons are cylinder in form, the dose distribution has angular dependence, as shown in FIG. 27. Continuous rotation of the balloons during PIII treatment would provide the most homogenous surface hardness. However, if this is not possible, turning the balloons three times (120 degrees each time) provides a reasonable homogeneity, with only a 10 percent deviation in the surface hardness. To prepare the balloon samples described above, the three turns method is employed.

Another reason for surface hardness inhomogeneity is plasma variation and corresponding variations of the ion current near the treated surface. This effect is caused by plasma density variations in volume and the charging effect of the polymer surface during high voltage pulse. This effect can be greatly reduced by positioning an additional electrode over balloon samples. For this purpose, a metal grid is utilized that is in electrical communication with the sample holder. This arrangement allows ions to pass through the grid on their way to the balloon surface. Dose distribution can be mapped using UV-vis spectra from LDPE film. Such a mapping is shown in FIG. 28.

Figure 28:
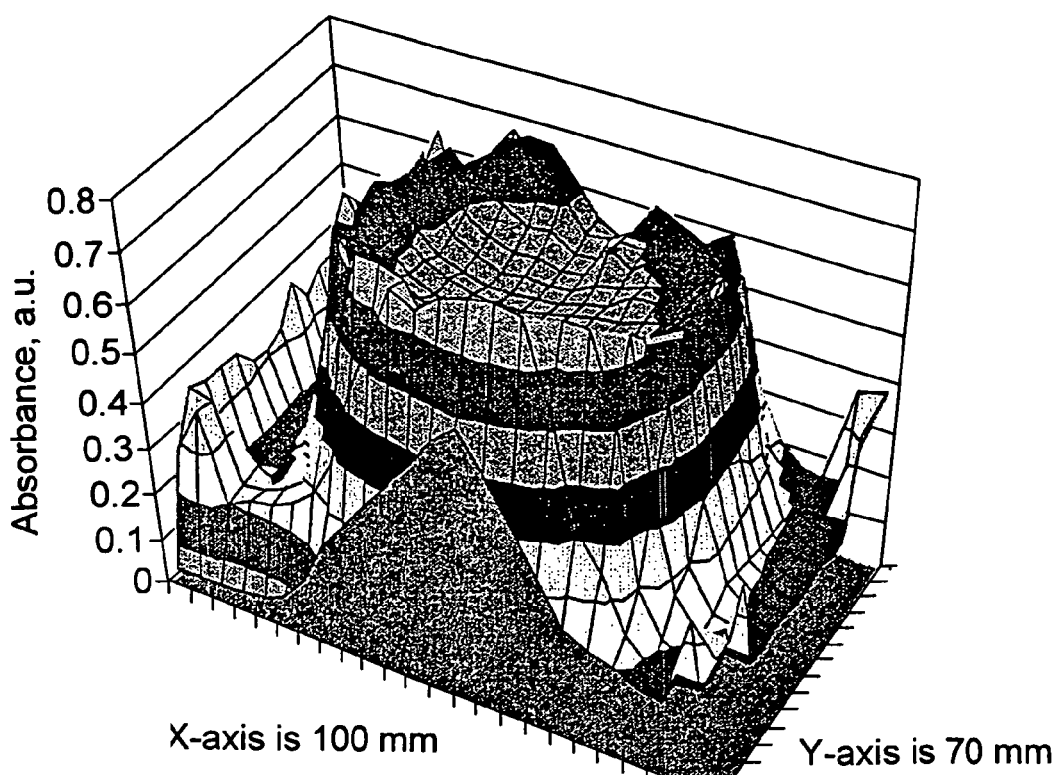
FIG. 28 shows a dose distribution for a PIII apparatus having an additional electrode.
Figure 29:
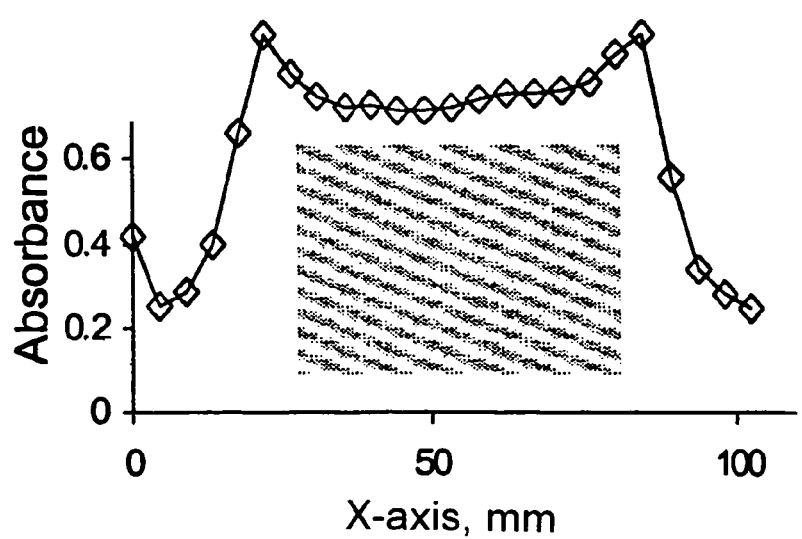
FIG. 29 is the dose distribution of FIG. 28 in an X-Y plane.

As shown in FIGS. 28 and 29, the central part of the sample holder provides a dose that does not vary by more than 10%. The size of central part depends on size of additional electrodes. In the case of absence of the additional electrode, the dose distribution is uncontrolled. In the samples discussed above, the area of homogenous dose has a diameter of approximately 50 mm. The balloons discussed above are all treated in the central portion of the sample holder.

Withdrawal, Burst, Torque and Securement for Unmodified and Modified Balloons

The table below provides data for balloon withdrawal, burst, torque and securement for unmodified and modified balloons. The modified balloons are treated with PIII as described above using a dose of $10^{16}$ ions/cm$^2$ at 30 keV.

| BALLOON PROPERTY PEBAX 7033 ® | UNMODIFIED BALLOON | MODIFIED BALLOON |
| --- | --- | --- |
| Balloon Withdrawal Force | 115 grams | 81 grams |
| Average Burst Pressure | 293 PSI | 294 PSI |
| Torque | 1.07 N(mm) | 1.26 N(mm) |
| Securement | 0.50 LB | 0.96 LB |

Balloon withdrawal force is measured using the method outlined by Devens, published U.S. Patent Application Publication No. 2004/0210211, the entire disclosure of which is hereby incorporated by reference herein in its entirety. Briefly, balloon withdrawal force is measured by determining the force required to remove a balloon from a torturous path defined by a polymer tube. Forces on the catheter and the tube can be measured by a series of transducers, as described by Devens. Torque is measured by turning the balloon in the same torturous path as used for the balloon withdrawal force test, and determining the resistance to rotation. Average burst strength is measured by determining an inflation pressure at which the balloon bursts at 20° C., as described in Wang, U.S. Pat. No. 6,171,278, and Levy, U.S. Pat. No. 4,490,421, the entire disclosure of each of which is hereby incorporated by reference herein in its entirety. Securement is measured using ASTM F2393-04, the entire disclosure of which is hereby incorporated by reference herein in its entirety.

In embodiments, the balloons can be used in various vascular or nonvascular applications. Exemplary applications include neuro, carotid, esophageal, or ureteral.

After treatment, as described above, the balloon can be further processed, e.g., to include a further coating, e.g., a hydrogel, or a polymer matrix coating including a drug. In embodiments, a balloon can be treated with a drug, or a polymer matrix that includes a drug, and subsequently treated by ions to modify the drug, the matrix and/or underlying balloon. Such a treatment can enhance or retard release of the drug from the balloon. In embodiments, other medical devices, e.g., coextruded medical devices, such as coextruded shafts, are treated by ions, as described above.

Still further embodiments are in the following claims.

What is claimed is:

1. A medical balloon, comprising:
    a balloon wall having a base polymer system comprising
        a base polymer material with an integral modified
        region including a region of crosslinked base polymer material adjacent the base polymer material and a carbonized region of base polymer material adjacent the crosslinked region, the crosslinked region is thicker than the carbonized region, the integral modified region having a surface with a fractured surface morphology such that non-fractured islands defined by fracture lines in the surface and said non-fractured islands have an area not more than about 20 µm².

2. The medical balloon of claim 1, wherein the carbonized region includes diamond-like material.

3. The medical balloon of claim 1, wherein the carbonized region includes graphitic material.

4. The medical balloon of claim 1, wherein the crosslinked region is directly bonded to the carbonized base polymer material and to unmodified base polymer material.

5. The medical balloon of claim 1, including an oxidized region, the oxidized region being directly bonded to the carbonized material and exposed to atmosphere.

6. The medical balloon of claim 1, wherein the modified region extends from an exposed surface of the base polymer system.

7. The medical balloon of claim 1, wherein the modulus of elasticity of the base polymer system is within about +/−10% of the base polymer system without the modified region.

8. The medical balloon of claim 1, wherein the thickness of the modified region is about 10 to about 200 nm.

9. The medial balloon of claim 1, wherein the modified region is about 1% or less of the overall thickness of the base polymer system.

10. The medial balloon of claim 1, wherein a, hardness coefficient of the carbonized base polymer material is about 500 Vickers Hardness (kgf/mm²) or more.

11. The medical balloon of claim 1, wherein the base polymer system carries a therapeutic agent.

12. The medical balloon of claim 11, wherein the fracture lines have a width of less than about 10 µm and act as a reservoir and comprise the therapeutic agent.

13. The medical balloon of claim 1, wherein the base polymer system includes coextruded polymer layers.

14. The balloon of claim 1, wherein a compliancy of the balloon is less than 10 percent of an initial diameter of the balloon between an internal pressure from about 2 bar to about 15 bar.

15. A balloon catheter, comprising:
a balloon wall having a base polymer system comprising a base polymer material with an integral modified region including a region of crosslinked of base polymer material adjacent the base polymer material and a carbonized region of base polymer material adjacent the crosslinked region, the crosslinked region is thicker than the carbonized region, the integral modified region having a surface with a fractured surface morphology such that non-fractured islands defined by fracture lines in the surface and said non-fractured islands have an area not more than about 20 µm².

16. The balloon catheter of claim 15, wherein the balloon catheter is sized for use in the vascular system.

17. The balloon catheter of claim 16, wherein the balloon catheter is sized for use in the coronary arteries.

18. The balloon catheter of claim 15, wherein the balloon catheter includes a stent positioned over the balloon.

19. A medical device, comprising:
a base polymer system including coextruded polymers, the base polymer system including an interface of the coextruded polymers, the base polymer system comprising a base polymer material, the base polymer system having an integral modified region including a crosslinked region of base polymer material adjacent the base polymer material and a carbonized region of base polymer material adjacent the crosslinked region, the crosslinked region is thicker than the carbonized region, the integral modified region having a surface with a fractured surface morphology such that non-fractured islands defined by fracture lines in the surface and said non-fractured islands have an area not more than about 20 µm².

20. The medical device of claim 19, wherein the modified region includes an interface of the coextruded polymers.

21. The medical device of claim 19, wherein the medical device is a medical balloon.

22. The device of claim 21, including a stent about the medical balloon.

23. The device of claim 19, wherein the polymer system carries a therapeutic agent.

24. A medical balloon, comprising:
a balloon wall having a base polymer system comprising a base polymer material, the base polymer system having an integral modified region including a crosslinked region of base polymer material adjacent the base polymer material and a carbonized region of base polymer material adjacent the crosslinked region, the crosslinked region is thicker than the carbonized region, the integral modified region having a surface with a fractured surface morphology formed by a plurality of fracture lines, the fracture lines having a width of less than 10 µm.

25. The medical balloon of claim 24, wherein the carbonized region includes diamond-like material.

26. The medical balloon of claim 24, wherein the carbonized region includes graphitic material.

27. A medical balloon, comprising:
a balloon wall having a base polymer system comprising a base polymer material with an integral modified region including a crosslinked region of base polymer material adjacent the base polymer material and a carbonized region of base polymer material adjacent the crosslinked region, the crosslinked region is thicker than the carbonized region, the integral modified region having a surface with a fractured surface morphology such that non-fractured islands defined by fracture lines, said fracture lines have a width of less than 10 µm in the surface and said non-fractured islands have an area not more than about 20 µm², and said fracture lines act as a reservoir and lines comprise a therapeutic agent.

28. The medical balloon of claim 27 wherein said fracture lines have a width of not more than about 0.5 µm.

* * * * *